US008202715B2

(12) United States Patent
Nguyen et al.

(10) Patent No.: US 8,202,715 B2
(45) Date of Patent: Jun. 19, 2012

(54) CLONING, EXPRESSION AND USE OF ACID LYSOPHOSPHOLIPASES

(75) Inventors: Khanh Q. Nguyen, Reichelsheim (DE); Volker Marschner, Bickenbach (DE); Kornelia Titze, Mühltal (DE); Bruno Winter, Stuttgart (DE)

(73) Assignee: AB Enzymes GmbH, Darmstadt (DE)

( * ) Notice: Subject to any disclaimer, the term of this patent is extended or adjusted under 35 U.S.C. 154(b) by 439 days.

(21) Appl. No.: 12/311,267

(22) PCT Filed: Sep. 21, 2007

(86) PCT No.: PCT/EP2007/008256
§ 371 (c)(1),
(2), (4) Date: Jun. 4, 2009

(87) PCT Pub. No.: WO2008/040465
PCT Pub. Date: Apr. 10, 2008

(65) Prior Publication Data
US 2010/0119656 A1    May 13, 2010

(30) Foreign Application Priority Data

Oct. 2, 2006  (DE) .................. 10 2006 046 857

(51) Int. Cl.
C12N 9/20       (2006.01)
C12N 1/20       (2006.01)
C12N 15/00      (2006.01)
C07H 21/04      (2006.01)

(52) U.S. Cl. .................. 435/198; 435/252.3; 435/320.1; 536/23.2

(58) Field of Classification Search .................. 435/198, 435/252.3, 320.1; 536/23.2
See application file for complete search history.

(56) References Cited

U.S. PATENT DOCUMENTS

| 4,873,192 | A | 10/1989 | Kunkel |
| 5,264,367 | A | 11/1993 | Aalrust et al. |
| 5,378,623 | A | 1/1995 | Hattori et al. |
| 5,521,080 | A | 5/1996 | Hattori et al. |
| 5,538,874 | A | 7/1996 | Hattori et al. |

FOREIGN PATENT DOCUMENTS

| EP | 0 219 269 B1 | 4/1987 |
| EP | 0 513 709 A2 | 11/1992 |
| EP | 0 575 133 | 12/1993 |
| EP | 1131416 A1 | 9/2001 |
| JP | 3151879 | 6/1991 |
| WO | WO-98/18912 | 5/1998 |
| WO | WO-98/26057 | 6/1998 |
| WO | WO-98/31790 | 7/1998 |
| WO | WO-00/28044 | 5/2000 |
| WO | WO-00/32758 | 6/2000 |
| WO | WO-01/27251 A1 | 4/2001 |
| WO | WO-01/29222 A2 | 4/2001 |
| WO | WO-02/24881 A1 | 3/2002 |
| WO | WO-02/066622 A2 | 8/2002 |
| WO | WO-03/060112 A1 | 7/2003 |
| WO | WO-03/097825 A2 | 11/2003 |
| WO | WO-2004/097012 A2 | 11/2004 |
| WO | WO-2004/111216 A2 | 12/2004 |

OTHER PUBLICATIONS

A. Memon et al., "Phospholipase B activity in mycelia of *Aspergillus niger*", FEMS Microbiology Letters, vol. 18, pp. 15-18 (1983).

W.C. McMurray et al., "Phospholipid Metabolism", Department of Biochemistry, University of Western Ontario, London, Ontario, Canada, Copyright 1972, pp. 129-160.

H. Fyrst et al., "The *PLB2* Gene of *Saccharomyces cerevisiae* Confers Resistance to Lysophosphatidylcholine and Encodes a Phospholipase B/Lysophospholipase", Biochemistry, vol. 38, pp. 5864-5871 (1999).

N. Masuda et al., "Primary structure of protein moiety of *Penicillium notatum* phospholipase B deduced from the cDNA", Eur. J. Biochem, vol. 202, pp. 783-787 (1991).

K.S. Lee et al., "The *Saccharomyces cerevisiae PLB1* Gene Encodes a Protein Required for Lysophospholipase and Phospholipase B Activity", The Journal of Biological Chemistry, 269(31), pp. 19725-19730 (1994).

O. Merkel et al., "Characterization and Function in Vivo of Two Novel Phospholipases B/Lysophospholipases from *Saccharomyces cerevisiae*", The Journal of Biologycal Chemistry, 274(40), pp. 28121-28127 (1999).

Y. Watanabe et al., Cloning and sequencing of phospholipase B gene from the yeast *Torulaspora delbrueckii*, FEMS Microbiology Letters, vol. 124, pp. 29-34 (1994).

H. Oishi et al., "Purification and Characterization of Phospholipase B from *Kluyveromyces lactis*, and Cloning of Phospholipase B gene", Biosci. Biotechnol. Biochem, 63(1), pp. 83-90 (1999).

Y. Sugiyama et al., "Molecular cloning of a second phospholipase B gene, caPLB2 from *Candida albicans*", Medical Mycology, vol. 37, pp. 61-67 (1999).

D.S. Hirschberg, "A Linear Space Algorithm for Computing Maximal Common Subsequences", Commun. Assoc Comput Mach, vol. 18, pp. 341-343 (1975).

E.W. Myers et al., "Optimal alignments in linear space", CABIOS, 4(1), pp. 11-17 (1988).

K.M. Chao et al., "Aligning two sequences within a specified diagonal band", CABIOS, 8(5), pp. 481-487 (1992).

(Continued)

Primary Examiner — Tekchand Saidha
(74) Attorney, Agent, or Firm — Peter F. Corless; Christine C. O'Day; Edwards Wildman Palmer LLP

(57) ABSTRACT

The invention relates to a DNA sequence that encodes a polypeptide with lysophospholipase activity and was isolated from *Aspergillus* and sequences derived therefrom, polypeptides with lysophospholipase activity encoded by these sequences as well as the use of these polypeptides for improving the filterability of syrups consisting of wheat starch and for related applications.

12 Claims, 6 Drawing Sheets

OTHER PUBLICATIONS

Figure 4:
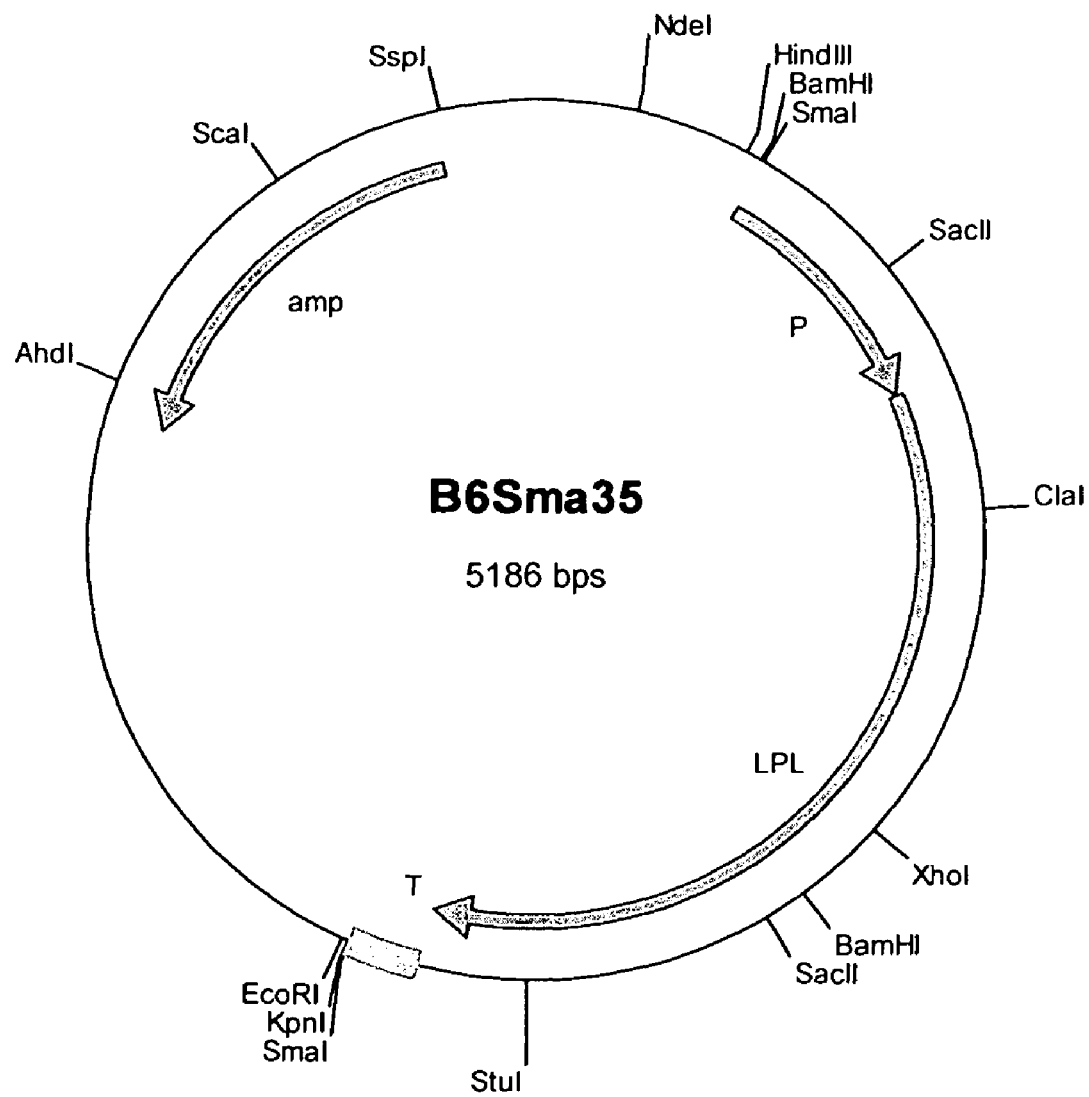

T.A. Kunkel et al., "Rapid and efficient site-specific mutagenesis without phenotypic selection", *Proc. Natl. Acad. Sci.*, vol. 82, pp. 488-492 (1985).

T.A. Kunkel et al., "Rapid and Efficient Site-Specific Mutagenesis without Phenotypic Selection", *Methods in Enzymology*, vol. 154, pp. 367-382 (1987).

F. Mooi et al., "The Use and Restriction Endonucleases and T4 DNA Ligase", *Techniques in Molecular Biology—MacMillan Publishing Company, New York*, Walker and Gaastra, pp. 199-219 (1983).

M.O. Dayhoff et al., "A Model of Evolutionary Change in Proteins", *Atlas of Protein Sequence and Structure*, Natl. Biomed. Res. Found., Washington, DC, pp. 345-352 (1978).

Sambrook et al., "Strategies for Cloning in Plasmid Vectors", *Molecular Cloning: A Laboratory Manual*, 2nd ed., Cold Spring Harbor Laboratory Press, Plainview, New York, (1989).

M. Penttila et al., "A versatile transformation system for the cellulolytic filamentous fungus *Trichoderma reesei*", Gene, vol. 61, pp. 155-164 (1987).

```
   1  CCCGGGGGCA  GTGCAACGGC  AGTGGTTATG  GTTCTGGTGG  CAGTGCTGGC
  51  GGGGGTGATT  CGGATGGTGC  ATACCAGGAT  GAACAAGAGG  CTGGAGGAGG
 101  ATGAAAGGGA  ACATGAAGTG  GAGCATCCAG  GTTTTAGATA  CATTCTATAA
 151  CTGTCTTTAT  AGTATTGAAC  ACATGCAGCT  GAATAGTGCT  GCCTGGACAG
 201  TGTGCATAAA  TTATCCGAAG  CAGCAAATGG  AAAAGATCAC  TGCCTAATGC
 251  CCAGCCCTGA  CGACAACACA  ACGTCTGGAA  TCAACCCTAG  ACAACCCACA
 301  TTCCCGCGGG  GACCGAAGCC  TAAATGATTG  GCAGTTCTTC  TGGCATTTCC
 351  ACTGTTCGTT  TTTCTATAGC  CATCCGATTC  GTGGAGAGGG  CCATCGGGAG
 401  ATGGGTCGAT  GATGATTTAC  GGCTGTCCCG  GAAGTATGTG  CTGACGCGGA
 451  GAACCGAGTA  TATCTACTAC  GTCAATGTTA  GCTATCCTTT  GGATTGGCAA
 501  TGTTCTTTCT  TTTGAGACAG  TGAGAGGTAT  CGACATGAAG  GCCATTTTCA
 551  CCCTTCTGAC  GGCCCTGGCC  GTAACGGCAA  CTCCTCTCGA  CCTGTCTATT
 601  CGAGCTCTCC  CCAACGCCCC  CAATGGCTAT  ACTCCGGCGA  ATGTGTCCTG
 651  TCCAGCGACA  CGACCCAGCA  TTCGCGGTGC  AGGGTCACTT  TCTCCGAATG
 701  AAACCGCCTG  GCTCCAGATC  CGTCGCAACA  ATACAGTCCA  GCCCATGAAG
 751  GACTTGCTGG  GCCGACTGAA  TCTCACCTTC  GACGCAGCGA  GCTACATCGA
 801  TCGCGTGTCG  AGTAACGTAT  CTAACCTGCC  TAATATCGCG  ATCGCTGTCT
 851  CTGGGGGTGG  ATACCGGGCT  CTGACCAATG  GAGCTGGAGC  TATAAAAGCC
 901  TTTGACAACC  GAACAAAAGG  CTCGACTGCA  CCTGGACAGC  TAGGGGGTCT
 951  ACTGCAGTCT  GCCACGTACG  TATCTGGACT  GAGCGGAGGA  GGATGGCTCG
1001  TGGGCTCAGT  GTATGTGAAC  AACTTCACGA  CCATCTCGGA  CCTCCAATCC
1051  GGAGGCAATG  GCGACGTATG  GCAGTTTTCC  ACGTCTATCC  TGGAAGGCCC
1101  CAAGACCAGA  CACCTGCAGT  TTCTATCCAC  AGTCGACTAC  TGGAGGAATT
1151  TGCTTGATGC  AGTCAACGGT  AAAAGCAACG  CGGGTTTCAA  CACCTCGCTA
1201  ACTGACTACT  GGGGCCGTGC  TCTATCCTAC  CAGTTCATCA  ACGATCCGAC
1251  TGGGAACGGC  GGGGTCAGCT  ACACCTGGTC  GTCCATCGCC  TTGAACGACA
1301  GCTTCCAGCG  CGGGGAGATG  CCACTCCCCA  TCCTGGTCGC  GGACGGCCGC
1351  AACCCAGGCG  AGCGGCTGAT  CGGCAGCAAC  TCGACCGTCT  ACGAGTTCAA
1401  CCCGTGGGAG  TTTGGCTCGT  TCGACCCGTC  CATCTTCGGC  TTTGCACCGC
1451  TCGAGTATCT  CGGCTCACGC  TTCGACAACG  GCCAGCTTCC  TAGCGGCGAA
1501  TCCTGCGTCC  GTGGTTTCGA  TAATGCAGGC  TTCGTCATGG  GCACCTCGTC
1551  CTCACTCTTC  AACCAGTTCA  TCCTGCGGCT  CAACACTACC  GATCTCCCGG
1601  ACCTGGTCAA  GGCGGCCTTC  TCCAGGATCC  TCACCGCGCT  AGGTCGGGAT
1651  GGCGACGATA  TCGCCATCTA  CGCCCCCAAC  CCGTTCTACG  GGTATCGCAA
1701  CTCGACCGCG  GTCTACTCGC  ACAGCCGCGA  GCTCGACGTC  GTCGACGGCG
1751  GCGAGGACGG  CCAGAATATC  CCCTTACACC  CCTCATCCA  GCCAACCCGC
1801  CACGTCGACG  TGATCTTCGC  GGTTGACTCC  TCGGCCGACA  CGGCGTACAA
1851  CTGGCCGAAT  GGGACCTCGC  TAGTCGCGAC  CTACGAGCGA  AGCCTCAACA
1901  GCTCGGGAAT  CGGCAATAGG  ACGGTCTTCC  CCGCCGTGCC  GGACGTGAAC
1951  ACCTTCGTCA  ACCTGGGCTT  GAACACCAGA  CCGACCTTCT  TCGGGTGCGA
2001  TCCCGCGAAT  CTGTCGGCGC  CGGCGCCCTT  GGTGGTATAC  CTGCCGAATG
2051  CGCCGTACAG  CGCGCATAGC  AACACCTCCA  CCTTCCAGTT  GTCGTACGCG
2101  GATTCCAGC  GCGATGAGAT  CATCACGAAT  GGGTATAACG  TTGTGACGCG
2151  GGGGAATGCA  ACCGCCGACA  AGGCCTGGCC  GAGCTGTGTG  GGGTGTGCCA
2201  TTCTGCAGCG  GTCGATGTAT  CGGACCAACA  CGTCCATGCC  GGCGGTGTGT
2251  TCCAGTTGCT  TCAAGGCGTA  TTGCTGGAAC  GGGACGGTGG  ATAGCAAGAC
2301  TCCTCGGACT  TATGAGCCGA  GCCAGGTGGT  GGGGAGTAAG  TCCACGTCTG
2351  CGGCTTACAG  GGAGGGTTGA  ATTGGCTGGT  GGGCGGGTTT  GCTGTTGGGC
2401  TGGGAGTGTG  GACAGTTTAG  ACAGATGGCA  TAAATCTATC  TCGCTGTTAT
2451  TTGCGCCATC  TACTCGCTAG  CACCTCTTCC  GTATACTGTA  GGTGCTAGCA
2501  TCCCGGG
```

Figure 1

```
  1  MKAIFTLLTA  LAVTATPLDL  SIRALPNAPN  GYTPANVSCP  ATRPSIRGAG
 51  SLSPNETAWL  QIRRNNTVQP  MKDLLGRLNL  TFDAASYIDR  VSSNVSNLPN
101  IAIAVSGGGY  RALTNGAGAI  KAFDNRTKGS  TAPGQLGGLL  QSATYVSGLS
151  GGGWLVGSVY  VNNFTTISDL  QSGGNGDVWQ  FSTSILEGPK  TRHLQFLSTV
201  DYWRNLLDAV  NGKSNAGFNT  SLTDYWGRAL  SYQFINDPTG  NGGVSYTWSS
251  IALNDSFQRG  EMPLPILVAD  GRNPGERLIG  SNSTVYEFNP  WEFGSFDPSI
301  FGFAPLEYLG  SRFDNGQLPS  GESCVRGFDN  AGFVMGTSSS  LFNQFILRLN
351  TTDLPDLVKA  AFSRILTALG  RDGDDIAIYA  PNPFYGYRNS  TAVYSHSREL
401  DVVDGGEDGQ  NIPLHPLIQP  TRHVDVIFAV  DSSADTAYNW  PNGTSLVATY
451  ERSLNSSGIG  NRTVFPAVPD  VNTFVNLGLN  TRPTFFGCDP  ANLSAPAPLV
501  VYLPNAPYSA  HSNTSTFQLS  YADSQRDEII  TNGYNVVTRG  NATADKAWPS
551  CVGCAILQRS  MYRTNTSMPA  VCSSCFKAYC  WNGTVDSKTP  RTYEPSQVVG
601  SKSTSAAYRE  G
```

```
   1 CCCGGGGGCA GTGCAACGGC AGTGGTTATG GTTCTGGTGG CAGTGCTGG
  51 GGGGGTGATT CGGATGGTGC ATACCAGGAT GAACAAGAGG CTGGAGGAGG
 101 ATGAAAGGGA ACATGAAGTG GAGCATCCAG GTTTTAGATA CATTCTATAA
 151 CTGTCTTTAT AGTATTGAAC ACATGCAGCT GAATAGTGCT GCCTGGACAG
 201 TGTGCATAAA TTATCCGAAG CAGCAAATGG AAAAGATCAC TGCCTAATGC
 251 CCAGCCCTGA CGACAACACA ACGTCTGGAA TCAACCCTAG ACAACCCACA
 301 TTCCCGCGGG GACCGAAGCC TAAATGATTG CAGTTCTTC TGGCATTTCC
 351 ACTGTTCGTT TTTCTATAGC CATCCGATTC GTGGAGAGGG CCATCGGGAG
 401 ATGGGTCGAT GATGATTTAC GGCTGTCCCG AAGTATGTG CTGACGCGGA
 451 GAACCGAGTA TATCTACTAC GTCAATGTTA GCTATCCTTT GGATTGGCAA
 501 TGTTCTTTCT TTTGAGACAG TGAGAGGTAT CGACATGAAG GCCATTTTCA
                                        m  k   a  i  f
 551 CCCTTCTGAC GGCCCTGGCC GTAACGGCAA CTCCTCTCGA CCTGTCTATT
      t  l  l   t  a  l  a   v  t  a  t   p  l  d  l   s  i
 601 CGAGCTCTCC CCAACGCCCC CAATGGCTAT ACTCCGGCGA ATGTGTCCTG
      r  a  l   p  n  a   p  n  g  y   t  p  a   n  v  s
 651 TCCAGCGACA CGACCCAGCA TTCGCGGTGC AGGGTCACTT TCTCCGAATG
       c  p  a  t   r  p  s   i  r   g  a  s  l   s  p  n
 701 AAACCGCCTG GCTCCAGATC CGTCGCAACA ATACAGTCCA GCCCATGAAG
       e  t  a   w  l  q  i   r  r   n  t  v   q  p  m  k
 751 GACTTGCTGG GCCGACTGAA TCTCACCTTC GACGCAGCGA GCTACATCGA
      d  l  l   g  r  l   n  l  t  f   d  a  a   s  y  i
 801 TCGCGTGTCG AGTAACGTAT CTAACCTGCC TAATATCGCG ATCGCTGTCT
      d  r  v  s   s  n  v   s  n  l   p  n  i   a  i  a  v
 851 CTGGGGGTGG ATACCGGGCT CTGACCAATG GAGCTGGAGC TATAAAAGCC
       s  g  g   g  y  r   a  l  t  n   g  a  g   a  i  k  a
 901 TTTGACAACC GAACAAAAGG CTCGACTGCA CCTGGACAGC TAGGGGGTCT
       f  d  n   r  t  k   g  s  t  a   p  g  q   l  g  g
 951 ACTGCAGTCT GCCACGTACG TATCTGGACT GAGCGGAGGA GGATGGCTCG
       l  l  q  s   a  t  y   v  s  g   l  s  g  g   g  w  l
1001 TGGGCTCAGT GTATGTGAAC AACTTCACGA CCATCTCGGA CCTCCAATCC
       v  g  s   v  y  v  n   n  f  t   t  i  s   d  l  q  s
1051 GGAGGCAATG GCGACGTATG GCAGTTTTCC ACGTCTATCC TGGAAGGCCC
       g  g  n   g  d  v  w   q  f  s   t  s  i   l  e  g
1101 CAAGACCAGA CACCTGCAGT TTCTATCCAC AGTCGACTAC TGGAGGAATT
       p  k  t  r   h  l  q   f  l  s   t  v  d  y   w  r  n
1151 TGCTTGATGC AGTCAACGGT AAAAGCAACG CGGGTTTCAA CACCTCGCTA
       l  l  d   a  v  n  g   k  s  n   a  g  f   n  t  s  l
1201 ACTGACTACT GGGGCCGTGC CTATCCTAC CAGTTCATCA ACGATCCGAC
       t  d  y   w  g  r  a   l  s  y   q  f  i   n  d  p
1251 TGGGAACGGC GGGGTCAGCT ACACCTGGTC GTCCATCGCC TTGAACGACA
       t  g  n   g  g  v  s   y  t  w   s  s  i   a  l  n  d
```

FIG. 3B

```
1301   GCTTCCAGCG CGGGGAGATG CCACTCCCCA TCCTGGTCGC GGACGGCCGC
        s  f  q   r  g  e  m   p  l  p   i  l  v   a  d  g  r
1351   AACCCAGGCG AGCGGCTGAT CGGCAGCAAC TCGACCGTCT ACGAGTTCAA
        n  p  g   e  r  l   i  g  s   n  s  t   v  y  e  f
1401   CCCGTGGGAG TTTGGCTCGT TCGACCCGTC CATCTTCGGC TTTGCACCGC
        n  p  w  e   f  g  s   f  d  p   s  i  f   g  f  a  p
1451   TCGAGTATCT CGGCTCACGC TTCGACAACG GCCAGCTTCC TAGCGGCGAA
        l  e  y   l  g  s   r  f  d   n  g  q   l  p  s   g  e
1501   TCCTGCGTCC GTGGTTTCGA TAATGCAGGC TTCGTCATGG GCACCTCGTC
        s  c  v   r  g  f   d  n  a   g  f  v   m  g  t  s
1551   CTCACTCTTC AACCAGTTCA TCCTGCGGCT CAACACTACC GATCTCCCGG
        s  s  l  f   n  q  f   i  l  r   l  n  t  t   d  l  p
1601   ACCTGGTCAA GGCGGCCTTC TCCAGGATCC TCACCGCGCT AGGTCGGGAT
        d  l  v   k  a  a  f   s  r  i   l  t  a   l  g  r  d
1651   GGCGACGATA TCGCCATCTA CGCCCCCAAC CCGTTCTACG GGTATCGCAA
        g  d  d   i  a  i   y  a  p   n  p  f   y  g  y  r
1701   CTCGACCGCG GTCTACTCGC ACAGCCGCGA GCTCGACGTC GTCGACGGCG
        n  s  t   a  v  y   s  h  s   r  e  l   d  v  v   d  g
1751   GCGAGGACGG CCAGAATATC CCCTTACACC CCTCATCCA GCCAACCCGC
        g  e  d   g  q  n  i   p  l  h   p  l  i   q  p  t  r
1801   CACGTCGACG TGATCTTCGC GGTTGACTCC TCGGCCGACA CGGCGTACAA
        h  v  d   v  i  f   a  v  d   s  s  a   d  t  a  y
1851   CTGGCCGAAT GGGACCTCGC TAGTCGCGAC CTACGAGCGA AGCCTCAACA
        n  w  p  n   g  t  s   l  v  a   t  y  e  r   s  l  n
1901   GCTCGGGAAT CGGCAATAGG ACGGTCTTCC CCGCCGTGCC GGACGTGAAC
        s  s  g   i  g  n  r   t  v  f   p  a  v   p  d  v  n
1951   ACCTTCGTCA ACCTGGGCTT GAACACCAGA CCGACCTTCT TCGGGTGCGA
        t  f  v   n  l  g   l  n  t  r   p  t  f   f  g  c
2001   TCCCGCGAAT CTGTCGGCGC CGGCGCCCTT GGTGGTATAC CTGCCGAATG
        d  p  a  n   l  s  a   p  a  p   l  v  v  y   l  p  n
2051   CGCCGTACAG CGCGCATAGC AACACCTCCA CCTTCCAGTT GTCGTACGCG
        a  p  y   s  a  h   s  n  t  s   t  f  q   l  s  y  a
2101   GATTCCCAGC GCGATGAGAT CATCACGAAT GGGTATAACG TTGTGACGCG
        d  s  q   r  d  e   i  i  t  n   g  y  n   v  v  t
2151   GGGGAATGCA ACCGCCGACA AGGCCTGGCC GAGCTGTGTG GGTGTGCCA
        r  g  n  a   t  a  d   k  a  w   p  s  c   v  g  c  a
2201   TTCTGCAGCG GTCGATGTAT CGGACCAACA CGTCCATGCC GGCGGTGTGT
        i  l  q   r  s  m  y   r  t  n   t  s  m   p  a  v  c
2251   TCCAGTTGCT TCAAGGCGTA TTGCTGGAAC GGGACGGTGG ATAGCAAGAC
        s  s  c   f  k  a   y  c  w  n   g  t  v   d  s  k
2301   TCCTCGGACT TATGAGCCGA GCCAGGTGGT GGGGAGTAAG TCCACGTCTG
        t  p  r  t   y  e  p   s  q  v   v  g  s   k  s  t  s
2351   CGGCTTACAG GGAGGGTTGA ATTGGCTGGT GGGCGGGTTT GCTGTTGGGC
        a  a  y   r  e  g  -
2401   TGGGAGTGTG GACAGTTTAG ACAGATGGCA TAAATCTATC TCGCTGTTAT
2451   TTGCGCCATC TACTCGCTAG CACCTCTTCC GTATACTGTA GGTGCTAGCA
2501   TCCCGGG
```

CLONING, EXPRESSION AND USE OF ACID LYSOPHOSPHOLIPASES

The invention relates to new DNA sequences that encode polypeptides having lysophospholipase activity. The invention also relates to new polypeptides having lysophospholipase activity. These polypeptides are acid phospholipases having high thermostability. Moreover, the invention relates to use of these lysophospholipases for improving the filterability of syrups consisting of wheat starch, improving doughs etc.

Phospholipids such as lecithin and phosphatidyl choline consist of glycerol esterfied with two fatty acids at the terminal (sn-1) position and the middle (sn-2) position of the glycerol and one ester-bound phosphate group at the third position (sn-3). The phosphate group itself may be esterfied with, e.g., amino alcohols. Phospholipases catalyze the hydrolysis of the acyl binding or the ester binding of phospholipids. There are different types of phospholipases differing in their cleavage pattern. Regarding the acyl cleaving phospholipases, it is distinguished between phospholipases A1 and A2, which hydrolyze the acyl group either at the sn-1 position or at the sn-2 position and produce lysophospholipids along the way. For this reason the remaining fatty acid may be hydrolyzed by the lysophospholipase (LPL). No position selectivity is known for the lysophospholipases.

Phospholipases of type B, which partly hydrolyze both acyl groups virtually simultaneously without the formation of an intermediate to the lysolecithin being observed, are described in literature (FEMS Microbiol. Let. 18 (1983) 15-18; Annu. Rev. Biochem. 41 (1972) 129-160). Such as for, e.g., the PLB1 and PLB3 activity of *Saccharomyces cerevisiae* (Biochemistry 1999 May 4; 38(18):5864-5871), this is often caused by the fact that the enzyme has much more LPL activity than $PLA_n$ activity. Pure lysophospholipases without phospholipase side activity may not cleave fatty acids from phospholipids having fatty acids at the positions sn-1 and sn-2.

The above-described lysophospholipases of type B, the amino acid sequence and/or nucleic acid sequence of which are/is known, can be divided in 2 groups. They are lysophospholipases that may additionally show very low phospholipase A activity.
a) The sequences of several enzymes with molecular weights of 45-100 kDa are known. They include the PLB from *Aspergillus niger* (WO 01/27251, WO 03/097825), the PLB from *Aspergillus fumigatus* (Shen et al. FEMS Microbiol Lett. 2004, 239 (1):87-93), the PLB from *Aspergillus oryzae* (WO 01/27251 & WO 01/29222), the PLB from *Fusarium venenatum* and *Fusarium verticillioides* (WO 00/28044), the PLB from *Penicillium notatum*, also referred to as *P. chrysogenum* (N. Masuda et al., Eur. J. Biochem., 202: 783-787 (1991)), the PLB 1-3 from *Saccharomyces cerevisiae* (Lee et al., 1994 J. Biol. Chem. 269: 19725-19730, Merkel et al., 1999 J. Biol. Chem. 274: 28121-28127), the PLB from *Torulaspora delbrueckii* (former designation: *Saccharomyces rosei*) (Watanabe et al., 1994, FEMS Microbiology Letters 124: 29-34), *Kluyveromyces lactis* (Oishi et al., 1999 Biosci. Biotechnol. Biochem, 63: 83-90), *Neurospora crassa* (EMBL O42791) and *Schizosaccharomyces pombe* (EMBL O13857).
b) Several sequences of enzymes with a molecular weight of 30-40 kDa are known. They include the lysophospholipase from *Aspergillus foetidus*, EP 0 808 903, the PLB from *A. niger*, WO 01/27251 and WO 03/097825, the PLB1 and PLB2 from *Candida albicans* (J. Biol. Chem. 273 (40): 26078-26086, 1998, Medical Mycology 37:61-67, 1998), and the PLB from *Pseudomonas* PS21, JP 03151879.

Furthermore, phospholipases of type A are mentioned in literature.
c) The group of the phospholipases of type A with a molecular weight of about 30-40 kDa. The following phospholipases from the state of the art are part of this group: WO 98/31790 (AB Enzymes GmbH) discloses that a suitable phospholipase A for degumming of edible oil was found in *Aspergillus niger*. The protein (36 kDa) only shows phospholipase activity after proteolytic cleavage, whereby the two fragments (30+6 kDa) remain connected via disulphide bridges. The enzyme cleaves lecithin into lysolecithin, but it is also able to cleave lysolecithin further, e.g., to phosphatidyl choline. WO 98/26057 discloses a phospholipase A from *Fusarium* sp. with a molecular weight of 29±10 kDa and an isoelectric point between pI 4.5-8. JP-10-155493 A2 discloses a phospholipase A1 from *A. oryzae* (295 aa); WO 02/24881 discloses a phospholipase A from the yeast *Zygosascus hellenicus* (407 aa) with an isoelectric point pI of about 4.2, and JP 03151879 discloses a bacterial phospholipase from *Pseudomonas* sp. with a molecular weight of about 30 kDa.

Moreover, EP 0 575 133 A2 (U.S. Pat. No. 5,538,874, U.S. Pat. No. 5,378,623, U.S. Pat. No. 5,521,080) discloses phospholipases A1 from *Aspergilli* with a molecular weight of 30-40 kDa and a pI of 2.8-4.5, however, without indicating sequence information. Furthermore; these patent specifications do not include any details or strategies to obtain the respective DNA by cloning.
d) The group of the phospholipases of type A with a molecular weight of about 60-100 kDa. It comprises: phospholipases from *Hyphozyma*, a yeast-like fungus, described in WO 98/18912, and phospholipases from *Aspergillus niger* as disclosed in WO 03/097825.

Furthermore, WO 2004/097012 discloses "core peptides" of known phospholipases A2 with increased phospholipase activity.

WO 00/32758, WO 03/060112 and WO 2004/111216 disclose methods to obtain enzyme variants that show a different lipase activity or phospholipase activity by means of "protein engineering" of known lipases, e.g., from *Thermomyces lanuginosus* and other phospholipases.

WO 02/066622 discloses new genes with high homology to the genes of the *Thermomyces lanuginosus* lipase as well as their use for gene shuffling to produce new lipolytic enzymes.

Lysophospholipases are used in the process of glucose syrup production and for further products derived therefrom to facilitate the separation of undesired components (see EP 0 219 269 B1). These components are separated by a filtration process, in which only cloudy filtrates are often obtained. By the use of lysophospholipases, not only the filtration rate but also the clearness of the filtrate may be positively influenced. Due to the high viscosity of the syrups (partial hydrolysate of starch, preferably partial hydrolysate of wheat starch) they must be stored and further processed at high temperatures. This requires enzymes with high temperature stability.

It is, therefore, the object of the present invention to provide proteins or polypeptides with improved lysophospholipase properties. The new lysophospholipases are to have a high ratio of lysophospholipase activity to phospholipase activity, in particular. These proteins with lysophospholipase activity are to have an increased thermostability, too.

Moreover, the proteins with lysophospholipase activity are to be produced simply, cost-efficiently and commercially. Furthermore, expression constructs according to the invention, which are suitable for the production of the proteins with lysophospholipase activity, are to be provided.

The aforementioned objects are solved by a DNA sequence that encodes a polypeptide with lysophospholipase activity characterized in that the DNA sequence is selected from a) DNA sequences that comprise a nucleotide sequence according to SEQ ID NO: 1, b) DNA sequences that comprise the encoding sequence according to SEQ ID NO: 1, c) DNA sequences that encode the protein sequence according to SEQ ID NO: 2, d) DNA sequences that are encoded by the plasmid B6Sma35 with the restriction map according to FIG. 4 and deposited under the accession number DSM 18370, e) DNA sequences that hybridize with one of the DNA sequences according to a), b), c) or d) under stringent conditions, f) DNA sequences that are related to the DNA sequences according to a), b), c), d) or e) due to the degeneracy of the genetic code, and g) strands complementary to the sequences according to a) to f).

The invention also relates to a polypeptide with lysophospholipase activity, selected from a) a polypeptide that is encoded by the coding part of one of the aforementioned DNA sequences, b) a polypeptide with the sequence according to SEQ ID NO: 2 or a sequence derived therefrom, which may be obtained by substitution, addition, deletion of one or more amino acid(s) therefrom, c) a polypeptide with a sequence that shows at least 89% identity to amino acids 16 to 611 of SEQ ID NO: 2, d) a polypeptide that is encoded by a nucleic acid sequence that hybridizes under stringent conditions with (i) the nucleotides 580 to 2367 of SEQ ID NO: 1, (ii) the cDNA sequence included in the nucleotides 580 to 2367 of SEQ ID NO: 1, (iii) a partial sequence of (i) or (ii) of at least 100 nucleotides, or (iv) a complementary strand of (i), (ii) or (iii), e) a variant of the polypeptide with SEQ ID NO: 2 comprising a substitution, deletion and/or insertion of one or more amino acid(s), f) allelic variants to the amino acid sequences a) to e).

Furthermore, the invention relates to expression constructs or hosts that are able to express polypeptides with lysophospholipase activity according to the invention. Moreover, the invention also relates the respective expression plasmids and vectors. Furthermore, the invention relates to the use of the polypeptides according to the invention for applications in the field of food technology, particularly for the processing of starch hydrolysis products from wheat starch.

The sequences of lysophospholipases mentioned in the above state of the art are expressis verbis excluded from the scope of protection of the invention. The sequences of the proteins with lysophospholipase activity as well as the respective DNA sequences of the following documents are particularly excluded from the scope of protection of the invention: WO 01/27251, WO 2004/111216, WO 2004/097012, WO 03/060112, WO 02/24881, WO 00/28044, WO 00/32758, WO 03/097825, EP 99 973 065.8 as well as corresponding divisional applications. The exclusion of the sequences refers to these documents in their entirety as well as individually and in any combination.

It was surprisingly found that a DNA sequence that encodes a polypeptide with lysophospholipase activity that has a high molecular weight, a high ratio of lysophospholipase activity to phospholipase activity and an increased thermostability may be isolated from a strain of the genus *Aspergillus fumigatus*. This lysophospholipase is an acid phospholipase deriving from a fungus with a molecular weight of about 64 to 78 kDa, which is able to hydrolyze fatty acid from lysolecithin, has a high ration of lysophospholipase activity to phospholipase activity and an increased thermostability and may be isolated from an organism of the genus *Aspergillus*.

Increased thermostability thereby means that the enzyme maintains an activity of at least 80% at a temperature of 65° C., pH 5 in the partial hydrolysate of wheat starch for at least 4 h.

The increased thermostability of the lysophospholipase of the invention was surprising as well as the high ratio of lysophospholipase activity to phospholipase activity and not obvious on the basis of the lysophospholipases described in the state of the art. These properties are neither described nor even rendered obvious by any of the naturally occurring lysophospholipases described in the state of the art.

Since there are no publications on thermostable lysophospholipases of filamentous fungi and, thus, also no indications as to which structural elements (helices, β-sheets, loops) must be especially designed in a lysophospholipase (existence of ionic interactions via charged amino acids, disulphide bridges, van-der-Waals interactions, hydrophobic interactions) to guarantee a high thermostability, it was not possible to predict that the detected lysophospholipase would have these properties. It not sufficiently known either where and how alterations in a lipolytic polypeptide must be carried out to obtain a high ratio of lysophospholipase activity to phospholipase activity. The genes of the family of the lipases in a broad sense, amongst which are also the phospholipases and lysophospholipases, show that small alterations in the sequence strongly influence the properties of the enzyme encoded by this sequence. This is shown, e.g., in the application WO 03/060112. This application discloses a method to produce variants of lipolytic enzymes. Alterations in the substrate specificity are thereby obtained by random mutagenesis and not by specific, directed mutations. This application also shows that despite high homology in the sequence, the property of the enzyme encoded by it cannot be predicted. This lacking correlation between DNA sequence and encoded enzyme as well as differences in the codon usage by the individual strains do not allow for deriving primers from known sequences to find new sequences with directed properties such as high thermostability, low lipase activity, high ratio of phospholipase activity to lysophospholipase activity and vice versa. Furthermore, due to the high homology between phospholipases and lysophospholipases it was not possible to predict that a lysophospholipase with the named properties is isolated by the selected batch. The regions that are possible for primer batches have short sequence parts of 2 to 3 conserved amino acids on the amino acid level with interruptions by variable amino acids. The variable amino acids have no tendency as to which amino acids are to be preferably found in phospholipases and which in lysophospholipases. Thus, together with the strain-specific codon usage there are consensus regions on the DNA level that may be used for a directed isolation of lysophospholipases. Therefore, it is not possible either to predict that the DNA regions selected for the primers are the part of the enzyme in which the specific amino acids coding for the named properties are localized. The selected primer batches were not congruent with known lysophospholipases. Thus, it is all the more surprising that the found polypeptide shows a high ratio of lysophospholipase activity to phospholipase activity.

The phospholipase sequence according to the invention and SEQ ID NO: 1 was compared to lysophospholipase sequences of the state of the art. The sequence SEQ ID: 1 shows the highest identity of 88% with the sequence PLB3 from *Aspergillus fumigatus* CBS 14489 (Shen et al., FEMS Microbiol. Letters 2004, 239 (1): 87-93). A high matching on the level of the amino acid sequence was also found for sequence 13 of the amino acid sequence from *Aspergillus niger* (68%) of WO 03/097825 as well as for LPL1 from *Aspergillus oryzae*, WO 01/027251 (73%). Moreover, the enzyme according to the invention is also characterized by a high ratio of lysophospholipase activity to phospholipase activity as compared to the enzymes described in the state of the art.

Thus, the invention also relates to polypeptides with lysophospholipase activity with a sequence that has at least 89% identity to the sequence according to SEQ ID NO: 1. The invention preferably relates to a polypeptide with lysophospholipase activity with a sequence that has at least 89% identity to amino acids 16 to 611 of SEQ ID NO: 1. The degree of identity is preferably at least 90%, more preferred at least 93%, even more preferred at least 95% and particularly preferred at least 98% provided that the respective sequences show lysophospholipase activity.

The degree of sequence identity is thereby determined in such a way that the number of residues of the shorter sequence that is involved in the comparison and has a "corresponding" counterpart in the other sequence is determined. For the purposes of the present invention the identity is thereby preferably determined in the usual manner by means of the usual algorithms. According to the invention, only the cDNAs or amino acids of the respective mature proteins are used for the comparison. Similar, preferably identical, sequence counterparts were determined according to the invention as homologue sequences by means of known computer programs. An example of such a program is the program Clone Manager Suite, which includes the program part Align Plus and is distributed by Scientific & Educational Software, Durham, N.C., U.S.A. A comparison between two DNA sequences or amino acid sequences as defined above is thereby carried out under the option local alignment either according to the FastScan-MaxScore method or according to the Needleman-Wunsch method, keeping the default values. The program version "Clone Manager 7 Align Plus 5" with the functions "Compare Two Sequences/Local Fast Scan-Max Score/Compare DNA sequences" or for amino acids "Compare Two Sequences/Global/Compare sequences as Amino Acids" was particularly used to calculate the identity according to the invention. The algorithms made available by the following sources were thereby used: Hirschberg, D. S. 1975. A linear space algorithm for computing longest common subsequences. Commun Assoc Comput Mach 18:341-343; Myers, E. W. and W. Miller. 1988. Optimal alignments in linear space. CABIOS 4:1, 11-17; Chao, K-M, W. R. Pearson and W. Miller. 1992. Aligning two sequences within a specified diagonal band. CABIOS 8:5, 481-487.

The invention further relates to addition molecules and/or deletion molecules of the aforementioned polypeptides with lysophospholipase activity. Thus, a polypeptide with lysophospholipase activity modified according to the invention may be elongated by adding further sequences at the N-terminal and/or C-terminal end, whereby the thus obtained amino acid sequences have to show lysophospholipase activity. Hybrid molecules, which have further advantageous properties, may be thereby produced. For example, suspension proteins or their native precursor forms may be added to proteins largely secreted, which further increases secretion efficiency. Moreover, active sequence segments of other enzymes may be added to produce enzymes with multiple specificity. Furthermore, polar and non-polar sequences may be added to influence the solubility properties or the mobility across a membrane of the thus obtained enzyme in a desired way.

Sequence segments of the polypeptide with lysophospholipase activity may also be deleted according to the invention, maintaining the lysophospholipase activity. The mutations, elongations and truncations may be conducted in a way known per se and using methods well known in the state of the art. Truncated polypeptides are often characterized by an increased secretion height compared to the full-length polypeptides. They may also show higher thermostabilities compared to the full-length polypeptide, since they only contain the "compressed core".

The production of such variants is generally known in the state of the art. For example, amino acid sequence variants of the polypeptides may be produced by mutation in the DNA. Processes for mutagenesis and changes in the nucleotide sequence are well known in the state of the art (cf., for example, Kunkel, Proc. Natl. Acad. Sci. USA, 82:488 (1985), Kunkel et al., Methods in Enzymol., 154:367 (1987), U.S. Pat. No. 4,873,192, Walker and Gaastra, eds., Techniques in Molecular Biology, Mac Millan Publishing Company, New York (1983)). Details on appropriate amino acid substitutions that do not negatively influence the biological activity of the protein of interest can be found in the model by Dayhoff et al., Atlas of Protein Sequence and Structure, Natl. Biomed. Res. Found., Washington, D.C. (1978). Conservative substitutions such as the replacement of an amino acid by another with similar properties are preferred. These replacements may be divided into 2 main groups with altogether 4 subgroups, and a replacement in each subgroup is referred to as conservative replacement, which does preferably not influence the activity or the folding of the protein.

| aliphatic | non-polar | G A P |
| | | I L V |
| | polar and uncharged | C S T M N Q |
| | polar and charged | D E |
| | | K R |
| aromatic | | H F W Y |

The terms "protein", "peptide" and "polypeptide" are primarily used interchangeably. A polypeptide or enzyme with phospholipase activity or a phospholipase is to refer to an enzyme that catalyzes the release of fatty acids from phospholipids, for example, lecithins. The phospholipase activity may be determined by use of any assay known per se and using one of these substrates.

A polypeptide or enzyme with lysophospholipase activity or a lysophospholipase is to refer to an enzyme that catalyzes the release of fatty acid from lysophospholipids, e.g., lysolecithins. The lysophospholipase activity may be determined by means of any assays known per se in which one of these substrates is used.

In connection with the polypeptides according to the invention the terms "phospholipase" or phospholipase A are to refer to enzymes with phospholipase A1 activity as well as phospholipase A2 activity. Phospholipase A1 or A2 is thereby defined according to the standard enzyme EC classification as EC 3.1.1.2 or 3.1.1.4.

Phospholipase B or lysophospholipase are polypeptides according to the standard is enzyme EC classification EC 3.1.1.5.

The invention also relates to DNA sequences that encode a polypeptide with lysophospholipase activity, comprising mutations, modifications or variations of the sequence according to SEQ ID NO: 1. Furthermore, the invention also relates to sequences that hybridize with the aforementioned sequences under relaxed or stringent conditions. The following conditions are considered as stringent: hybridization at 65° C., 18 h in dextran sulphate solution (GenescreenPlus, DuPont), subsequently washing of the filters for 30 min each, first with 6×SSC, twice 2×SSC, twice 2×SSC, 0.1% SDS and finally with 0.2×SSC at 65° C. (membrane transfer and detection methods, Amersham).

Furthermore, the invention also relates to DNA sequences that are related to the above sequences according to the invention due to the degeneracy of the genetic code as well as allelic variants thereof. The degeneracy of the genetic code may thereby result from the natural degeneracy or an especially selected codon usage. Naturally occurring allelic variants may be identified by means of well-known techniques of molecular biology such as, for example, the polymerase chain reaction (PCR) and hybridization techniques.

The invention also relates to a process for the production of a polypeptide with lysophospholipase activity using recombinant techniques comprising the breeding of recombinant prokaryotic and/or eukaryotic host cells that comprise a DNA sequence according to the invention under conditions that support the expression of the enzyme as well as the subsequent recovery of the enzyme. The invention also relates to the use of the polynucleotide sequences according to the invention for the production of probes to detect similar sequences that encode respective enzymes in other organisms as well as for the transformation of host cells.

A DNA sequence that encodes a polypeptide according to the invention may be used to transform any host cells such as, for example, cells of fungi, yeasts, bacteria, plants or mammals. Cells transformed in such a way are characterized by a secretion of the lysophospholipase according to the invention. The thus produced lysophospholipase enzyme causes an efficient hydrolysis of the fatty acids from lysophospholipids.

The invention also relates to expression cassettes that may be used to introduce the DNA sequence encoding a lysophospholipase according to the invention or an open reading frame into a host cell. They preferably comprise a transcription start region that is connected with the open reading frame. Such an expression cassette may comprise a variety of restriction cleavage sites for inserting the open reading frame and/or other DNAs, e.g., a transcription regulator region and/or selectable marker genes. The transcription cassette comprises in 5'→3' direction of the transcription a transcription start region and a translation start region, the DNA sequence of interest and a transcription stop region and translation stop region that is functional in a microbial cell. The termination region may be native regarding the transcription initiation region, may be native regarding the DNA sequence of interest and may be derived from any other source.

The term "open reading frame" (ORF) refers to the amino acid sequence that is encoded between the translation start codons and translation stop codons of a coding sequence. The terms "start codon" and "stop codon" refer to a unit of three contiguous nucleotides (codons) in a coding sequence, specifying the chain start and chain stop of the protein synthesis (mRNA translation).

In connection with a nucleic acid "operative linkage" refers to a compound as a part of the same nucleic acid molecule in an appropriate position to and orientation on the transcription start of the promoter. DNA in operative linkage to a promoter is located under the transcription initiation regulation of the promoter. Coding sequences may be operatively linked with the regulator sequence in sense orientation or antisense orientation. Regarding polypeptides, operative linkage means the connection as part of the same polypeptide, i.e., via peptide bindings.

According to the invention, any promoter may be used. Promoter usually refers to the nucleotide sequence upstream (5') to the coding sequence and controls the expression of the coding sequence by providing the recognition of the RNA polymerase and other factors that are necessary for the correct transcription. The promoter used according to the invention may comprise a minimal promoter, i.e., a short DNA sequence from a TATA box and other sequences that specify the transcription start site to which regulator elements are attached for expression control.

The promoter used according to the invention may also comprise a nucleotide sequence that comprises a minimal promoter and regulator elements and may control the expression of a coding sequence or functional RNA. This type of promoter sequence consists of proximal and distal elements located upstream, whereby the elements named last are often referred to as enhancers. Consequently, an enhancer is a DNA sequence that may stimulate the promoter activity and may be an element inherent to the promoter or an inserted heterologous element to improve the expression height or tissue specificity of a promoter. It may function in both orientations and may even work if it is located upstream or downstream to the promoter. Not only enhancers but also other upstream located promoter elements bind DNA-binding proteins mediating their effects. Promoters may be derived from a native gene in their entirety or my be composed of different elements derived from different naturally occurring promoters or can even be composed of synthetic DNA segments. A promoter may also comprise DNA sequences that are involved in the binding of protein factors that control the efficiency of the transcription initiation as response to physiological or development-related conditions.

Promoter elements, particularly TATA elements, that are inactive or have a strongly reduced promoter activity in the absence of an upstream activation are referred to as minimal promoters or core promoters. In the presence of an appropriate transcription factor or appropriate transcription factors the function of the minimal promoter is the enabling of the transcription. Thus, a minimal promoter or core promoter only consists of all basic elements that are necessary for the transcription initiation, e.g., a TATA box and/or an initiator.

The invention also relates to vector constructs comprising DNA sequences according to the invention. These vector constructs comprise any plasmid, cosmid, phage or other vector in double-stranded or single-stranded, linear or circular form, which might also be transmittable or mobilizable themselves and may either transform a prokaryotic or eukaryotic host by integration into the cellular genome or are extrachromosomally present (e.g., autonomously replicating plasmids with replication origin).

Vectors, plasmids, cosmids, artificial yeast chromosomes (YACs), artificial bacterial chromosomes (BACs) and DNA segments to be used for the transformation of cells generally comprise the DNA that encode the phospholipase according to the invention as well as another DNA such as cDNA, a gene or genes that is/are to be introduced into the cells. These DNA constructs may comprise further structures such as promoters, enhancers, polylinkers or also regulator genes, if necessary. One of the DNA segments or genes that was/were selected for the cellular introduction conveniently codes/code a protein that is expressed in the thus obtained transformed (recombinant) cells, which leads to a screenable or selectable property and/or provides the transformed cell with an improved phenotype.

The construction of vectors that may be used according to the invention is known to a person skilled in the art due to aforementioned disclosure and the general expert knowledge An expression cassette according to the invention may comprise one or several restriction site(s) to put the polynucleotide that encodes the lysophospholipase under the control of a regulator sequence. The expression cassette may also comprise a termination signal in operative linkage with the polynucleotide as well as regulator sequences that are necessary for the proper translation of the polynucleotide. The expression cassette that comprises the polynucleotide according to the invention may be chimeric, i.e., at least one of its components is heterologous relating to at least one of the other components. The expression of the polynucleotide in the expression cassette may be under control of a constitutive promoter, an inducible promoter, a regulated promoter, a viral promoter or a synthetic promoter.

The vectors may already comprise regulator elements, e.g., promoters, or the DNA sequences according to the invention may be manipulated in such a way that they comprise such elements. Appropriate promoter elements that may be used are known in the state of the art and are, for example, for *Trichoderma reesei* the cbh1 promoter or cbh2 promoter, for *Aspergillus oryzae* the amy promoter, for *Aspergillus niger* the xyl promoter, glaA promoter, alcA promoter, aphA promoter, tpiA promoter, gpdA promoter, sucl promoter and pkiA promoter. Appropriate promoter elements that may be used for expression in yeast are known in the state of the art and are, for example, the pho5 promoter or the gap promoter for expression in *Saccharomyces cerevisiae* and for *Pichia pastoris*, for example, the aoxl promoter or the fmd promoter, or the mox promoter for *H. polymorpha*.

DNA that is appropriate for introduction into cells may also comprise, besides the DNA according to the present invention, DNA that was derived or isolated from any source. An example of a derived DNA is a DNA sequence that was identified in a given organism as a useful fragment and then chemically synthesized in a basically pure form. An example of such a DNA is an appropriate DNA sequence that was, for example, obtained by the use of restriction endonucleases, so that it may be further manipulated according to the invention, for example, amplified. The amdS gene from *Aspergillus nidulans*, which may be used as a marker gene, and its regulatory sequences as well as polylinkers are among those, inter alia.

Such a DNA is usually referred to as recombinant DNA. Thus, an appropriate DNA comprises completely synthetic DNA, semi-synthetic DNA, DNA isolated from biological sources and DNA derived from channelled RNA. Generally, the introduced DNA is no original constituent of the genotype of the recipient DNA, however, according to the invention, a gene may also be isolated from a given genotype and optionally altered and subsequently multiple copies of the gene may be introduced into the same genotype, e.g., to increase the production of a given gene product.

The introduced DNA comprises without limitation DNA from genes such as, for example, of bacteria, yeasts, fungi or viruses. The channelled DNA may comprise modified or synthetic genes, parts of genes or chimeric genes including genes of the same or a different genotype. For example, DNA of the plasmids pUC18, pUC19 may also be included here.

The DNA used according to the invention for the transformation may be circular or linear, double-stranded or single-stranded. In general, the DNA is a chimeric DNA such as a plasmid DNA, which also comprises coding regions that are flanked by regulator sequences and support the expression of the recombinant DNA present in the transformed cell. For example, the DNA itself may comprise or consist of a promoter that is active in a cell, that is derived from a source differing from the cell, or a promoter that is already present in the cell, i.e., the transformation target cell, may be used.

In general, the introduced DNA is relatively small, less than about 30 kb, to minimize the sensitivity to physical, chemical or enzymatic degradation, which increases with the size of the DNA.

The selection of an appropriate expression vector depends on the host cells. Yeast expression vectors or fungi expression vectors may comprise a replication origin, an appropriate promoter and enhancer as well as any necessary ribosome binding sites, polyadenylation sites, splice donor sites and splice acceptor sites, transcription termination sequences and non-transcribed 5'-flanking sequences.

Examples of appropriate host cells are: fungi cells of the genus *Aspergillus, Rhizopus, Trichoderma, Neurospora, Mucor, Penicillium* etc. such as, for example, yeasts of the genera *Kluyveromyces, Saccharomyces, Schizosaccharomyces, Trichosporon, Schwanniomyces, Hansenula, Pichia* and the like. Appropriate host systems are, for example, fungi such as *Aspergilli*, e.g., *Aspergillus niger* (ATCC 9142) or *Aspergillus ficuum* (NRLL 3135) or *Trichoderma* (e.g., *Trichoderma reesei* QM6a), and yeasts such as *Saccharomyces*, e.g., *Saccharomyces cerevisiae* or *Pichia* such as, e.g., *Pichia pastoris* or *Hansenula*, e.g., *H. polymorpha* (DSMZ 70277). Such micro-organisms may be obtained from established depositary institutions, e.g., the American Type Culture Collection (ATCC), the Centraalbureau voor Schimmelcultures (CBS) or the Deutschen Sammlung für Mikroorganismen and Zellkulturen GmbH (DSMZ) or any other depositary institution.

The expression cassette may include a transcription start region and translation start region of the polynucleotide according to the invention in the 5'-3' transcription direction and a transcription region and termination region that are functional in vivo or in vitro. The termination region may be native regarding the transcription initiation region or may be native or of other origin regarding the polynucleotide. The regulator sequences may be located upstream (5' non-coding sequences), inside (introns) or downstream (3' non-coding sequences) of a coding sequence and influence the transcription, the RNA processing or the stability and/or the translation of the associated coding sequence. Regulator sequences may comprise without limitation enhancers, promoters, repressor binding sites, translation leader sequences, introns or polyadenylation signal sequences. They may comprise natural and synthetic sequences as well as sequences that are combined of synthetic and natural sequences.

The vector used according to the invention may also comprise appropriate sequences for the amplification of the expression.

Examples of promoters that may be used according to the invention are promoters of which is known that they control the expression in the eukaryotic cells. Any promoter with the ability to express in filamentous fungi may be used. Examples are a promoter that is strongly induced by starch or cellulose, e.g., a promoter for glucoamylase or α-amylase from the genus *Aspergillus* or cellulase (cellobiohydrolase) from the genus *Trichoderma*, a promoter for enzymes in the glycolytic metabolic pathway such as, for example, phosphoglycerate kinase (PGK) and glycerol aldehyde-3-phosphate-dehydrogenase (GPD) etc. The cellobiohydrolase-I promoter, the cellobiohydrolase-II promoter, the amylase promoter, the glucoamylase promoter, the xylanase promoter or the enolase promoter is preferred.

In addition to the use of a special promoter, other types of elements may influence the expression of transgenes. It was particularly demonstrated that introns have the potential to increase transgene expression.

The expression cassette may comprise further elements, for example, such elements that may be regulated by endogenous or exogenous elements such as zinc finger proteins, including naturally occurring zinc finger proteins or chimeric zinc finger proteins.

The expression cassette used according to the invention may also comprise enhancer elements or upstream promoter elements.

Vectors for the use according to the invention may be constructed in such a way that they comprise an enhancer element. Thus, the constructs according to the invention comprise the gene of interest together with a 3' DNA sequence, which acts as a signal to terminate the transcription and to allow for the polyadenylation of the thus obtained mRNA. Any signal sequence that makes the secretion from the selected host organism possible may be used. A preferred signal sequence is the lysophospholipase signal sequence from *Aspergillus fumigatus* or signal sequences derived therefrom for the secretion from filamentous fungi.

A special leader sequence may also be used, since the DNA sequence between the transcription start site and the start of the coding sequence, i.e., the non-translated leader sequence, may influence the gene expression. Preferred leader sequences comprise sequences that control the optimal expression of the adhered gene, i.e., they comprise a preferred consensus leader sequence, which increases or maintains the mRNA stability and prevents an inappropriate translation initiation. The selection of such sequences is well known to the person skilled in the art.

To improve the possibility to identify the transformants, a selectable or screenable marker gene may be incorporated in the expression cassette. Such marker genes are well known to a person skilled in the art.

The expression cassette or a vector construct that comprises the expression cassette is introduced into a host cell. A variety of techniques is available and well known to a person skilled in the art of channelling constructs into a host cell. The transformation of microbial cells may be carried out by means of polyethylene glycol, calcium chloride, viral infection, DEAE dextran, phage infection, electroporation and other methods known in the state of the art. The transformation of fungi may be carried out according to Penttilä et al., Gene 61:155-164, 1987. The introduction of a recombinant vector into yeasts may be carried out according to methods known per se, including electroporation, use of spheroplasts, lithium acetate and the like.

As soon as the expression cassette or the DNA sequence according to the invention is obtained, it may be introduced into vectors according to processes known per se to overexpress the encoded polypeptide in appropriate host systems. However, DNA sequences as such may also be used to transform appropriate host systems of the invention to obtain an over-expression of the encoded polypeptide.

As soon as a DNA sequence according to the invention is expressed in an appropriate host cell in an appropriate medium, the encoded lysophospholipase may be concentrated and/or isolated either from the medium if the lysophospholipase is secreted into the medium or from the host organism if the lysophospholipase is intracellularly present, e.g., in the periplasmic space, according to processes known per se. Known processes for the separation of the insoluble components of the culture medium and the biomass followed by processes for concentrating the lysophospholipase may be used to produce concentrated lysophospholipase solutions or to prepare the drying of the lysophospholipase. For example, filtration processes or centrifugation processes may be used to separate the insoluble components, followed by ultrafiltration processes for concentration, or cross flow filtration processes are used. The drying may be carried out by freeze drying, spray drying, granulation processes, extrusion or other processes. Known processes of protein purification may be used to isolate the lysophospholipases according to the invention. For example, different chromatographic or gel-chromatographic processes may be used individually or in combination. Depending on the host cell used in a recombinant production process, the enzyme according to the invention may or may not be covalently modified by glycosylation. In eukaryotic cells the glycosylation of the secreted proteins provide a basis for modulation of the protein folding, the conformation stability, the thermal stability and the resistance against proteolysis. As regards a specific application of the lysophospholipase, a glycosylated variant of the enzyme may be preferred to a non-glycosylated variant.

The invention also relates to isolated or basically purified nucleic acid compositions and protein compositions. An isolated and purified polynucleotide/polypeptide or segment thereof refers to a polynucleotide or polypeptide or segment thereof that is isolated from its native environment and is present in a purified form for further use. An isolated polynucleic acid segment or polypeptide may be present in a purified form and may be present in a non-native environment such as, for example, in a transgenic host cell. For example, an isolated or purified polynucleotide segment or protein or a biologically active part thereof is basically free from further cellular material or culture medium if produced according to recombinant techniques or is basically free from chemical precursors or other chemical compounds. An isolated polynucleotide is preferably free from sequences (preferably protein-encoding sequences) that naturally flank the nucleic acid (i.e., sequences that are localized at the 5' ends and 3' ends of the nucleic acid) in the genomic DNA of the organism from which the nucleic acid is derived. For example, according to different embodiments, the isolated nucleic acid molecule may comprise less than about 5 kb, 4 kb, 3 kb, 2 kb, 1 kb, 0.5 kb or 0.1 kb of nucleotide sequences that naturally flank the nucleic acid molecule in the genomic DNA of the cell from which the nucleic acid is derived. A protein that is basically free from cellular material comprises compositions of protein or polypeptide with less than about 70%, 50%, 30%, 20%, 10%, 5% (based on the dry weight) of contaminating protein. If the protein according to the invention or a biologically active fragment thereof is recombinantly produced, the culture medium preferably comprises less than about 70%, 50%, 30%, 20%, 10%, 5% (based on the dry weight) of the chemical precursors or non-protein-like chemical substances.

The invention also relates to lysophospholipase compositions that comprise the polypeptide according to the invention. Lysophospholipase compositions are generally liquid or dry. Liquid compositions preferably comprise the lysophospholipase enzyme in a purified or enriched form. However, auxiliary agents such as, for example, a stabilizer and/or glycerol, sorbitol or monopropylene glycol, additives such as salts, sugar, preservatives, agents to adjust the pH value and proteins may be added. Typical liquid compositions are aqueous or oily slurries.

Dry compositions may be freeze-dried, spray-dried, granulated or extruded compositions, which may only comprise the enzyme. Dry compositions may be granulates that may easily be mixed with other components. Preferably, the particle size of the enzyme granulate is compatible with the one of the other components of the mixture. This allows for save and purposeful agents to incorporate enzymes in combined products, for example.

A food additive according to this embodiment of the present invention may be combined with other food components in a similar way, whereby processed food products are produced. Such other food components comprise one or more enzyme supplements, vitamins, minerals and trace elements. Then the thus obtained combined dietary supplement may be mixed with other food components such as grain and plant proteins in an appropriate amount to obtain processed food. The processing of these components to processed food may be carried out by means of processing devices known per se.

In a preferred embodiment the lysophospholipase compositions according to the invention additionally comprise an effective amount of one or more enzyme(s) for food or animal feed or for the application in pre-stages of the production of food or animal feed, preferably selected from alpha-galactosidases, beta-galactosidases, laccases, other phospholipases, phosphatases, endoglucanases, particularly endo-beta-1,4-glucanases, endo-beta-1,3(4)-glucanases, endo-1,2-betaglucanases and endo-1,3-alpha-glucanases, cellulases, xylosidases, galactanases, particularly arabinogalactan-endo-1,4-beta-galactosidases and arabinogalactan-endo-1,3-beta-galactosidases, pectin-degrading enzymes, particularly pectinases, pectinesterases, pectinlyases, polygalacturonases, arabananases, rhamnogalacturonases, rhamnogalacturonanacetylesterases, rhamnogalacturonan-alpha-rhamnosidases, pectate lyases and alpha-galacturonidases, mannanases, beta-mannosidases, mannan acetylesterases, xylan acetylesterases, proteases, xylanases, arabinoxylanases, lipolytic enzymes such as lipases, digalactosid-diglycerol esterases and cutinases, and other enzymes such as laccases and transglutaminases.

The lysophospholipases according to the invention may be used for a variety of applications. Examples are applications in the processing of hydrolysates of wheat starch or as catalysts for the transesterification of lysophospholipids.

The lysophospholipases according to the invention may also be used in the preparation of dough for bread doughs or cake doughs to improve the elasticity of the bread or the cake, for example. Thus, the lysophospholipase may be added to the dough during the preparation, followed by the steps of kneading the dough, forming the dough and baking.

The lysophospholipase may also be used together with phospholipases for degumming oil, e.g., in a method as it is described, for example, in the patent EP 0 513 709 B2 (Röhm GmbH/Metallgesellschaft AG, today AB Enzymes GmbH/mg technologies ag).

The gene for the lysophospholipase that was isolated from the micro-organism *Aspergillus fumigatus* was deposited in the plasmid B6Sma35 under accession number DSM 18370 at the Deutschen Sammlung von Mirkoorganismen und Zellkulturen GmbH (DSMZ), Mascheroder Weg 1b, D-38124 Braunschweig on Jun. 14, 2006 in accordance with the provisions of the Budapest Treaty.

The invention is further described on the basis of the enclosed figures. It is shown in:

FIG. 1: The nucleotide sequence of the chromosomal lysophospholipase gene from the strain *Aspergillus fumigatus* RH3949 (SEQ ID NO: 1).

FIG. 2: The amino acid sequence of the lysophospholipase gene from the strain *Aspergillus fumigatus* RH3949 (SEQ ID NO: 2).

FIGS. 3A-B: The nucleotide sequence of the chromosomal lysophospholipase gene from the strain *Aspergillus fumigatus* RH3949 (SEQ ID NOs: 1 and 2) and amino acid sequences derived therefrom.

FIG. 4: The restriction map of the vector B6Sma35.

Figure 5:
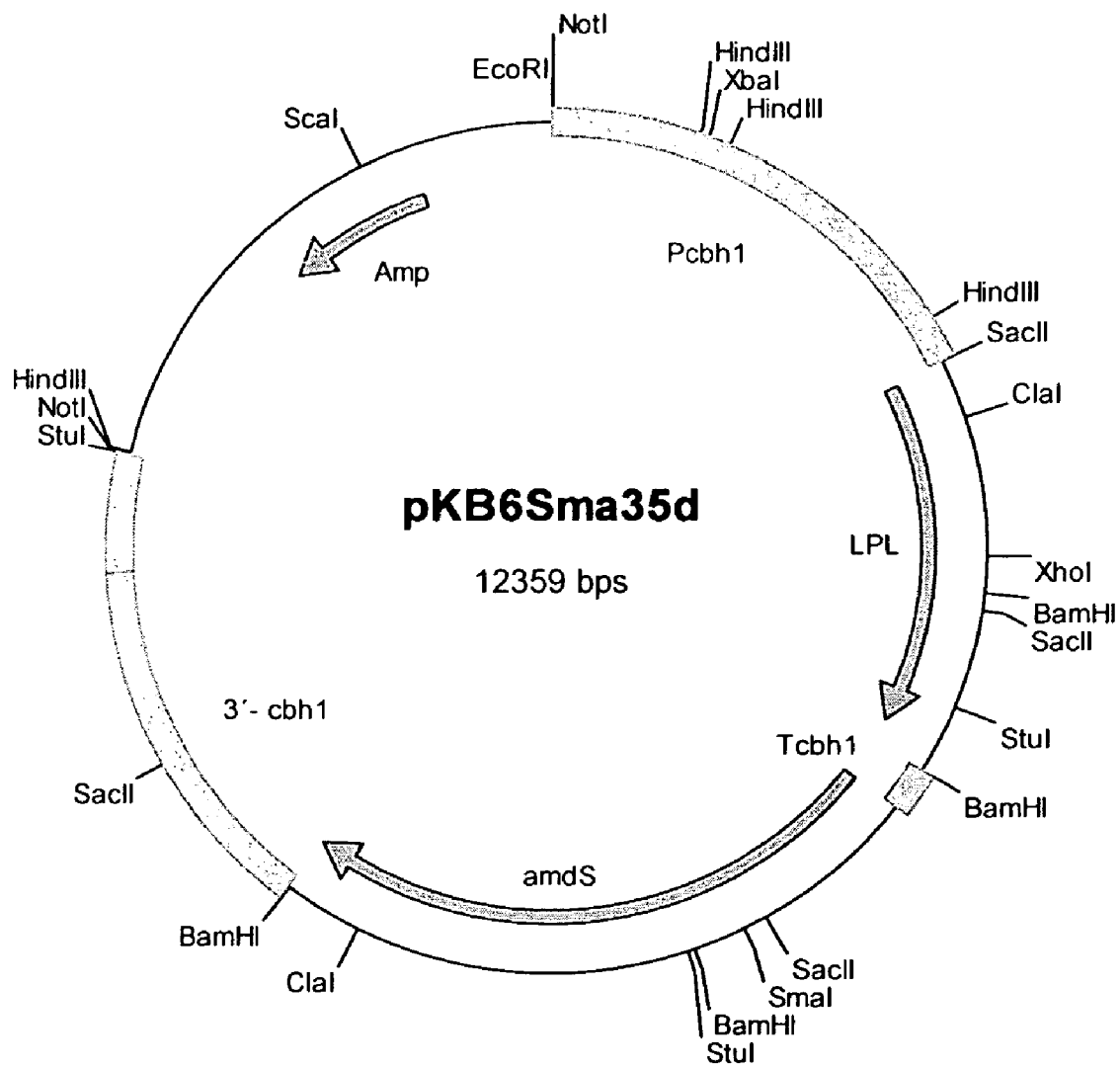

FIG. 5: The restriction map of the expression vector pKB6Sma35d.

The following examples will specify the invention in detail:

REFERENCE EXAMPLE 1

Determination of the Lysophospholipase Activity 1 unit LPL corresponds to the amount of enzyme that results in a hydrolysis rate of 1 micromol per minute in a 0.01 molar aqueous solution of lysolecithin at pH 4.5 and 55° C.

To determine the lysophospholipase activity, a mixture of 0.25 ml L-lysophosphatidyl choline by Sigma Type 1, cat. no. L4129 [solubilize 10 mg L-lysophosphatidyl choline in 1 ml distilled water (20 mmol)], 0.250 ml 0.02 M sodium acetate buffer pH 4.5 and 0.1 ml enzyme dilution is incubated in distilled water at 55° C. for 10 min. Buffer and substrate solution are pre-incubated for 5 min at 55° C. Samples are taken after 1 min and after 10 min of reaction time, and the released fatty acids are determined by means of the optimized enzymatic color test for the determination of free fatty acids (Non-Esterfied Fatty Acids, NEFA, reference number 1383 175 by the company Boehringer-Mannheim). The period between the 1st and the 2nd sampling is used as reaction time.

REFERENCE EXAMPLE 2

Determination of the Phospholipase Activity 1 unit phospholipase corresponds to the amount of enzyme that releases 1 μmol fatty acid from phosphatidyl choline per minute under standard conditions.

Reagents:
Substrate Solution:

1 g Epikuron 200 (purified phosphatidyl choline from soy by LUCAS MEYER, reference number 139029), 100 ml deionized water and 5 ml 0.32 M $CaCl_2$ solution are homogenized by means of an Ultra Turrax for 2 min at 24,000 rpm. The substrate solution is stable at 4°-8° C. for 3-4 d.

Other Solutions:

0.32 M $MgCl_2$ solution, fresh 3.3 mM citric acid-monohydrate solution, 10 mM is KOH solution, 1% Triton X100 (company Fluka) solution in demineralized water.

Enzyme Solution

The enzyme preparations are solved in deionized water. The enzyme concentration in the batch may not exceed 2.5 U $g^{-1}$.

Carrying Out the Determination
Main Values 10 ml substrate solution
10 ml 1% Triton X100 solution
5 ml 3.3 mM citric acid-monohydrate solution are pipetted in a 25 ml wide-necked Erlenmeyer flask and tempered at 40° C. for 10 min. The pH value adjusts to 3.3-3.5.

After adding 0.1 ml of enzyme solution, the analysis batch is incubated at 40° C. for 10 min. When the incubation time is over, it is titrated to pH 10.0 with 0.01 M KOH, whereby the first 5 ml KOH are added rapidly (duration: about 1 min). The consumption of KOH is registered.

Blank Test

The enzyme parent solution is heated at 95° C. for 15 min and, thus, deactivated. After cooling down to room temperature, the further treatment is the same as for the main values.

An incubation of the blank samples is not necessary.
Evaluation:

$$PLU/g = \frac{\Delta V_{KOH} * c_{KOH} * 1000}{\Delta t * c_s * v}$$

| | | |
|---|---|---|
| $v_{KOH}$ | [ml] | difference in consumption between the blank value and the main value |
| $c_{KOH}$ | [mol l$^{-1}$] | concentration of KOH |
| $t$ | [min] | incubation time |
| $c_S$ | [g ml$^{-1}$] | concentration of the sample |
| $v$ | [ml] | volume used |

EXAMPLE 1

Preparation of Lysophospholipase Using *Aspergillus fumigatus*

*Aspergillus fumigatus* RH3949 was grown in 200 ml shaking flasks filled with 50 ml medium at 28° C., 200 rpm, over 5 d. The medium consisted of 0.5% Epikuron 200 (Lucas Meyer), 0.5% corn steep powder, 0.2% NH$_4$NO$_3$, 100 mM KH$_2$PO$_4$ and 0.1% Triton X100. The pH value was adjusted to pH 6 before sterilisation. The medium was inoculated with a spore suspension. After 5 days, the culture supernatant was separated from the mycelium by filtration, and the lysophospholipase activity in the liquid was measured.

EXAMPLE 2

Cloning and Expression of the Lysophospholipase (lpl) Gene from the *Aspergillus fumigatus* Strain RH3949 a) DNA First Strand Synthesis

About 1×10$^7$ spores of the *A. fumigatus* strain RH 3949 were inoculated in 100 ml medium (3.75% Glucidex, 3% corn steep powder, 0.5% (NH$_4$)$_2$HPO$_4$), and cultivated at 45° C. for 2 to 3 days. The obtained mycelium was used for the RNA preparation by means of the Qiagen column (RNeasy Mini Plant Kit, Qiagen).

The cDNA first-strand synthesis was carried out according to the specifications of the manufacturer (BRL). 4 µl 5×BRL buffer (250 mM Tris/HCl, pH 8.3, 375 mM KCl, 15 mM MgCl$_2$), 1 µl 10 mM dNTP, 2 µl 100 mM DTT, 50 pmol primer EA13, 1 µl RNA (2 µg total RNA) and 2,000 U RTase Super Script (BRL) were pipetted together in a 20 µl reaction batch. The reaction batch was incubated at 45° C. for 50 min.

For the later amplification of the phospholipase cDNA by polymerase chain reaction, the batch was diluted with 20 µl bidistilled water and stored at −20° C.

The DNA sequence of the primer EA13 is:

(SEQ ID NO: 3)
5'-gAC TCg AgT CgA CAT CgA (T)$_{20}$ (A/C/g)-3' b) Amplification of a Partial Sequence of Lysophospholipase cDNA by Polymerase Chain Reaction (PCR)

Different oligoprimers for the amplification of the lysophospholipase cDNA were derived by comparing the lysophospholipase amino acid sequences of *S. cerevisiae* (Lee et al., J. Biol. Chem., 1994, 269, 19725-19730), *P. notatum* (Masuda et al., 1991, Eur. J. Biochem., 202, 783-787) and *Aspergillus awamori* RH3312. It was found that the primer pair 3949/875 and 3949/4710iv leads to the correct lysophospholipase cDNA gene fragment.

3949/875
5'-GAT GGC GGC GAG GAT GGA CAG AA-3'    (SEQ ID NO: 4)

3949/8710iv
5'-AGT GCC GTT CCA GCA ATA-3'           (SEQ ID NO: 5)

The amplification of a partial sequence of lysophospholipase cDNA was carried out with the batch of the cDNA first-strand synthesis by the PCR method. The reaction batch of 100 µl comprised: 10 µl 10× buffer (200 mM Tris/HCl, pH 8.4, 500 mM KCl), 2 µl 10 mM dNTP, each 50 µmol oligoprimer, 1 µl of the batch of the 1st strand cDNA, 5 U Taq DNA polymerase (BRL). The batch was treated for denaturation at 95° C. for 5 min, followed by 45 cycles (95° C. for 1 min, 45° C. for 1 min, 72° C. for 1 min), and subsequently the extension was carried out at 72° C. for 5 min.

The PCR products were purified on the column (Concert Rapid PCR Purification System, Gibco, BRL) and cloned in pGEMT plasmid (Promega).

One transformant comprises the correct partial sequence of the lysophospholipase cDNA and was referred to as 3949/19/16.

c) Cloning of the chromosomal lysophospholipase (lpl) Gene from the Strain RH3949

The preparation of chromosomal DNA was carried out according to a specification by Hynes, M. J et al. (1983) Mol. Cell. Biol. 3, 1430-1439.

After partial hydrolysis with Sau3A I, the DNA was fractioned according to size by means of a saccharose density gradient centrifugation. Fractions that contained DNA fragments of 9-20 kb were combined and precipitated with ethanol at −20° C. After washing and drying, the DNA was inserted in EMBL3 DNA hydrolyzed by BamHI/EcoRI and packaged in vitro. Packaging in the phage lysate Gigapack II Gold Packaging was carried out according to the specification described by the manufacturer (Stratagene Instruction Manual).

To identify the chromosomal lysophospholipase gene in a lambda EMBL3 gene bank, the cDNA fragment from the plasmid 3949/19/16 was used as radioactive gene probe. The hybridization was carried out at 65° C. for 18 h in dextran sulphate solution (GenescreenPlus, DuPont). After hybridization, the filters were washed each for 30 min, first with 6×SSC, twice 2×SSC, twice 2×SSC, 0.1% SDS and subsequently with 0.2×SSC at 65° C. (membrane transfer and detection methods, Amersham).

Six positive clones were identified. From the results of the analysis with the restriction endonucleases and southern hybridization, the phage DNA of the clone B6 was hydrolyzed with SmaI. The 2.5 kb SmaI fragment inserted in pUC18 was referred to as B6Sma35 (FIG. 4). The nucleotide sequence of the 2.5 kb DNA fragment and the amino acid sequence derived therefrom were determined (SEQ ID NOs: 1 and 2).

The gen comprises 2,507 bp, a signal peptide of 15 amino acids: Met Lys Ala Ile Phe Thr Leu Leu Thr Ala Leu Ala Val Thr Ala (Prediction of Protein Localization Sites, PSORT, Nakai and Kanehisa, 1992, Genomics 14, 897-911) and has a calculated molecular weight of 64,068 Da. A comparison of the amino acid sequences between *A. fumigatus* lysophospholipase according to the invention and the published PLB3 lysophospholipase from *A. fumigatus* shows an identity of 88% (BLAST determination, http://www.ncbi.nlm.gov/blast. Altschul Stephen F., et. al. (1997), Gapped BLAST and PSI-Blast: A new generation of protein database search programs, Nucleic Acids Res. 25, 3389-3402).

d) Construction of Expression Vector pKB6Sma35D

First the N-terminal region of the lysophospholipase gene was amplified by the PCR method. The primers used therefor have the following sequences:

```
B6Sma3
                                       (SEQ ID NO: 6)
5'-GAA TTC CGC GGA CTG CGC ATC ATG AAG GCC ATT TTC
ACC CTT CTG AC-3'

B6Sma4
                                       (SEQ ID NO: 7)
5'-TGA GGA TCC TGG AGA AGG CCG CCT TG-3'
```

The polymerase chain reaction took place under the following conditions: denaturation at 95° C. for 5 min, 45 cycles at 95° C. for 1 min, 45° for 1 min, 72° C. for 1 min and extension for 5 min at 72° C. The reaction batch of 100 µl contained: 10 µl 10×PCR buffer (200 mM Tris/HCl, pH 8.4, 500 mM KCl), 3 µl 50 mM $MgCl_2$, 2 µl 10 mM dNTP (each 10 mM dATP, dCTP, dGTP and dTTP), 50 pmol oligoprimer, 10 ng plasmid DNA as matrix and 5 U Taq-DNA polymerase (BRL). The PCR product was purified, hydrolyzed by the enzymes SacII/BamHI and inserted into plasmid pALK487, which was cleaved by the same enzymes. By the sequencing of the obtained plasmid pKB6Sma35b, the correctness of the cloning was confirmed. In the same process the C-terminal region of the gene was amplified by the primer pair B6Sma5 and Sma35/5. The sequence of the primers is:

```
Sma35/5
                                       (SEQ ID NO: 8)
5'-ATG GGC ACC TCG TCC TCA CTC TTC-3'

B6Sma5
                                       (SEQ ID NO: 9)
5'-CGG GAT CCT AGC ACC TAC AG TAT ACG GAA G-3'
```

After the hydrolysis with BamHI, the PCR product was incorporated into the plasmid pKB6Sma35b, which was cleaved by the same enzyme. The resulting plasmid with the designation pKB6Sma35c, which comprises the entire lysophospholipase (lpl) gene under control of the *T. reesei* cbhI promoter, was prepared and sequenced.

By incorporating the EcoRI, fill-in/SpeI, fill-in fragment from the plasmid pALK424, which comprises the selection marker amdS, into the plasmid pKB6Sma35c cleaved by the enzyme SmaI, the expression vector pKB6Sma35d was constructed (FIG. 5).

e) Transformation of the *T. reesei* Strain RH31013

The DNA used for transformation was isolated from the vector pKB6Sma35d as NotI fragment. This NotI fragment contained the lysophospholipase gene under control of the *T. reesei* cbhI promoter and the selection marker amdS.

For isolating the 9.3 kb fragment, the vector pKB6Sma35d was electrophoretically separated in 1.2% LowMelting agarose after hydrolysis with NotI. The agarose gel, which contained the 9.7 kb NotI DNA fragment, was digested with β-agarose I (Biolabs), and then the DNA was precipitated with isopropanol. Between 10 to 15 µg DNA fragment are needed for the transformation.

The transformation in *T. reesei* RH 31013 was carried out according to the specification by Penttilä M., et al. (1987, Gene 61, 155-64).

The 13 transformants obtained after transformation were purified twice over single spore colonies on selection plates and finally transferred to PD medium (potato dextrose agar). The transformants RH31202 and RH31204 were used for further experiments.

EXAMPLE 3

Recombinant Production of LPL from *A. fumigatus* RH3949

The growing of the transformants RH31202 and RH31204 was carried out in 250 ml shaking flasks without baffle, with 50 ml medium (3% lactose, 3% distillers spent grain, 5% $K_2HPO_4$, 0.5% $(NH_4)_2SO_4$ and 1% corn steep powder, pH value 4.4). The medium was inoculated with a spore suspension.

After 6 days of incubation at 28° C., 200 rpm, 25 mm deflexion, the culture supernatant was separated from the mycelium by sterile filtration and used for the further experiments.

EXAMPLE 4

Characterization of the Recombinantly Produced Lpl from *A. fumigatus*

The lysophospholipase activity and the phospholipase activity of the sterilely filtrated culture solutions of RH31202 and RH31204 were determined according to Reference Examples 1 and 2.

TABLE 1

Enzyme Activities of the Culture Supernatants of RH 31202 and RH 31204, Which Express the Lysophospholipase of *A. fumigatus* RH 3949

| strain | [LPL $g^{-1}$] | [PLU $g^{-1}$] | [LPL/PLU] |
|---|---|---|---|
| RH 31013 | 3 | 1 | 3 |
| RH 31202 | 22618 | 153 | 148 |
| RH 31204 | 22860 | 152 | 150 |

The recombinantly produced lysophospholipase from *Aspergillus fumigatus* RH3949 has a very high ratio of LPL to PL activity. The enzyme hardly shows phospholipase activity. This is not the case for the phospholipases B described in is literature. The latter show a lower ratio of LPL to PL activity than the enzyme according to the invention.

EXAMPLE 5

Improvement of the Filterability of Maltose Syrup

The recombinantly produced LPL from *Aspergillus fumigatus* RH3949 was used in further experiments on the improvement of the filtration of partial hydrolysates of wheat starch (abbreviated to syrup).

Part A

Partial hydrolysate of wheat starch by the company Cerestar/Cargil (wheat B-starch) was incubated with enzymes of the culture supernatants of Example 3 at 60° C. and 65° C. for up to 4 h at pH 4. The partial hydrolysate of the wheat starch was therefor adjusted to pH 4 by HCl. 100 ml partial hydrolysate of wheat starch were incubated in 200 ml Erlenmeyer flasks with the LPL of Example 4 at a dosage of 280 LPL per kg syrup, and the solution was stirred with a magnetic stirrer. During and at the end of the incubation time the result was visually examined. The appearance of flakes, which leave a clear solution if influenced by lysophospholipase, shows the effect of the enzyme compared to the untreated syrup, which remains cloudy. The flocculation was semiquantitatively divided into the steps: very good, good, bad, no alteration. The supernatant cooled down to 35° C. was subsequently filtrated through a paper filter (Whatman No. 4), and the filtration was thereby determined after 2.5 and 10 min. The clearness of the filtrate was photometrically determined at 720 nm.

By adding the lysophospholipase according to the invention, good flocculation was already visible after 1 h; in the blank test without enzyme addition there was no is flocculation even after 4 h, and the batch remained cloudy. After 4 h the flocculation in the batch with enzyme was very good.

By adding the lysophospholipases according to the invention, the filtration rate of the enzymatically treated syrup was also clearly increased as can be seen in Table 2.

TABLE 2

Treatment of Partial Hydrolysate of Wheat Starch with Lysophospholipase at Different Temperatures

| enzyme | temperature [° C.] | dosage [LPL per kg syrup] | filtrate after 2.5 min [ml] | filtrate after 10 min [ml] |
|---|---|---|---|---|
| blank test | 60° C. | 0 | 7.5 | 11.5 |
| RH31202 | 60° C. | 280 | 11.0 | 17.5 |
| blank test | 65° C. | 0 | 8.0 | 13.0 |
| RH31202 | 65° C. | 280 | 14.0 | 23.0 |

Part B

In a further experiment not only the lysophospholipase according to the invention but also β-amylase was added to the partial hydrolysate of wheat starch, as it is carried out in the starch industry on an industrial scale. The pH value is thereby adjusted to pH 4.9 by HCl, and the incubation time is 6 h at 60° C. Then the flocculation was optically assessed, and the filtration rate was determined as carried out in part A. The results of the filtration test are summarized in Table 3.

TABLE 3

Treatment of Partial Hydrolysate of Wheat Starch with β-Amylase and Lysophospholipase at pH 4.9, 60° C. for 6 h.

| enzyme | filtrate after 2.5 min [ml] | filtrate after 10 min [ml] |
|---|---|---|
| blank test | 7.0 | 10.5 |
| only β-amylase | 14.5 | 25.0 |
| lysophospholipase and β-amylase | 19.5 | 33.0 |

The Added Amount of Lysophospholipase (RH 31202) Was 280 LPL Per kg Syrup.

The results show that also in the presence of β-amylase, which leads to a further decrease in the viscosity of the partial hydrolysate of wheat starch, a clear increase in the filtration rate is caused by adding the lysophospholipase according to the invention.

The addition of β-amylase does not lead to flocculation. Only by adding lysophospholipase, will a very good flocculation take place.

The filtrate with addition of β-amylase had an extinction of 0.116 AU at 720 nm, whereas the extinction of the filtrate dropped to 0.017 AU if lysophospholipase was added. This shows a distinct improvement of the clearness of the filtrate, caused by the addition of the lysophospholipase according to the invention.

The invention claimed is:

1. An isolated DNA sequence that encodes a polypeptide with lysophospholipase activity characterized in that the DNA sequence is selected from
   a) DNA sequences that comprise the nucleotide sequence of SEQ ID NO: 1,
   b) DNA sequences that comprise the coding sequence of SEQ ID NO: 1,
   c) DNA sequences that encode the protein sequence of SEQ ID NO: 2,
   d) DNA sequences that are encoded by the plasmid B6Sma35 deposited under accession number DSM 18370,
   e) DNA sequences that hybridize with one of the DNA sequences according to a), b), c) or d) under stringent conditions, wherein the stringent conditions are hybridization at 65° C. for 18 h in dextran sulphate solution, washing of the filter for 30 min each, first with 6×SSC, twice 2×SSC, twice 2×SSC, 0.1% SDS and 0.2×SSC at 65° C.,
   f) DNA sequences that are variants of any of the DNA sequences according to a), b), c), d) or e), wherein any variability is due to the degeneracy of the genetic code such that the variant encodes an identical protein sequence, and
   g) strands having a full complement of the DNA of a) to f).

2. The isolated DNA sequence according to claim 1 characterized in that the sequence is obtained from *Aspergillus*.

3. The isolated DNA sequence according to claim 2 characterized in that the sequence is obtained from *Aspergillus fumigatus*.

4. An isolated nucleic acid sequence that comprises an analogue of one of the sequences according to claim 1 wherein the sequence encodes a polypeptide with lysophospholipase activity and
   a) has at least 89% identity to one of these sequences or
   b) hybridizes with one of these sequences under stringent conditions, wherein the stringent conditions are hybridization at 65° C. for 18 h in dextran sulphate solution, washing of the filter for 30 min each, first with 6×SSC, twice 2×SSC, twice 2×SSC, 0.1% SDS and 0.2×SSC at 65° C., or
   c) is a strand having a full complement of the DNA of a) to b).

5. An expression construct that comprises the isolated DNA of claim 1 in operable linkage with one or more sequence(s) to control the expression of the polypeptide with lysophospholipase activity in an appropriate host cell.

6. The expression construct of claim 5 wherein the sequence to control the expression of the polypeptide is a promoter selected from the glucoamylase promoter or the α-amylase promoter of the genus *Aspergillus*, the cellulase (cellobiohydrolase) promoter of the genus *Trichoderma*, a promoter for an enzyme in the glycolytic metabolic pathway, the xylanase promoter or the enolase promoter.

7. The expression construct of claim 5, further comprising a secretory leader sequence.

8. A recombinant host cell transformed with the expression construct of claim 5.

9. The recombinant host cell of claim 8 obtained from a fungus cell of the genus *Aspergillus, Rhizopus, Trichoderma, Neurospora, Mucor* or *Penicillium* or a yeast cell of the genus *Kluyveromyces, Saccharomyces, Schizosaccharomyces, Trichosporon, Schwanniomyces, Hansenula* or *Pichia*.

10. A plasmid B6Sma35 deposited under accession number DSM 18370.

11. A process for the production of a polypeptide with lysophospholipase activity comprising culturing the host cell of claim 8 under conditions that support the expression of the polypeptide and recovering the polypeptide.

12. The expression construct of claim 5, wherein the promoter for an enzyme in the glycolytic metabolic pathway is phosphoglycerate kinase or glycerol aldehyde-3-phosphate dehydrogenase.

* * * * *

SEQUENCE LISTING

```
<160> NUMBER OF SEQ ID NOS: 9

<210> SEQ ID NO 1
<211> LENGTH: 2507
<212> TYPE: DNA
<213> ORGANISM: Aspergillus fumigatus
<220> FEATURE:
<221> NAME/KEY: CDS
<222> LOCATION: (535)..(2367)

<400> SEQUENCE: 1
cccgggggca gtgcaacggc agtggttatg gttctggtgg cagtgctggc ggggqtgatt     60 cggatggtgc ataccaggat gaacaagagg ctggaggagg atgaaaggga acatgaagtg    120
gagcatccag gttttagata cattctataa ctgtctttat agtattgaac acatgcagct    180
gaatagtgct gcctggacag tgtgcataaa ttatccgaag cagcaaatgg aaaagatcac    240
tgcctaatgc ccagccctga cgacaacaca acgtctggaa tcaaccctag acaacccaca    300
ttcccgcggg gaccgaagcc taaatgattg gcagttcttc tggcatttcc actgttcgtt    360
tttctatagc catccgattc gtggagaggg ccatcggag atgggtcgat gatgatttac    420
ggctgtcccg gaagtatgtg ctgacgcgga gaaccgagta tatctactac gtcaatgtta    480
```

```
gctatccttt ggattggcaa tgttctttct tttgagacag tgagaggtat cgac atg       537
                                                            Met
                                                            1 aag gcc att ttc acc ctt ctg acg gcc ctg gcc gta acg gca act cct       585
Lys Ala Ile Phe Thr Leu Leu Thr Ala Leu Ala Val Thr Ala Thr Pro
          5                  10                  15 ctc gac ctg tct att cga gct ctc ccc aac gcc ccc aat ggc tat act       633
Leu Asp Leu Ser Ile Arg Ala Leu Pro Asn Ala Pro Asn Gly Tyr Thr
         20                  25                  30 ccg gcg aat gtg tcc tgt cca gcg aca cga ccc agc att cgc ggt gca       681
Pro Ala Asn Val Ser Cys Pro Ala Thr Arg Pro Ser Ile Arg Gly Ala
     35                  40                  45 ggg tca ctt tct ccg aat gaa acc gcc tgg ctc cag atc cgt cgc aac       729
Gly Ser Leu Ser Pro Asn Glu Thr Ala Trp Leu Gln Ile Arg Arg Asn
 50                  55                  60                  65 aat aca gtc cag ccc atg aag gac ttg ctg ggc cga ctg aat ctc acc       777
Asn Thr Val Gln Pro Met Lys Asp Leu Leu Gly Arg Leu Asn Leu Thr
                 70                  75                  80 ttc gac gca gcg agc tac atc gat cgc gtg tcg agt aac gta tct aac       825
Phe Asp Ala Ala Ser Tyr Ile Asp Arg Val Ser Ser Asn Val Ser Asn
             85                  90                  95 ctg cct aat atc gcg atc gct gtc tct ggg ggt gga tac cgg gct ctg       873
Leu Pro Asn Ile Ala Ile Ala Val Ser Gly Gly Gly Tyr Arg Ala Leu
        100                 105                 110 acc aat gga gct gga gct ata aaa gcc ttt gac aac cga aca aaa ggc       921
Thr Asn Gly Ala Gly Ala Ile Lys Ala Phe Asp Asn Arg Thr Lys Gly
    115                 120                 125 tcg act gca cct gga cag cta ggg ggt cta ctg cag tct gcc acg tac       969
Ser Thr Ala Pro Gly Gln Leu Gly Gly Leu Leu Gln Ser Ala Thr Tyr
130                 135                 140                 145 gta tct gga ctg agc gga gga gga tgg ctc gtg ggc tca gtg tat gtg      1017
Val Ser Gly Leu Ser Gly Gly Gly Trp Leu Val Gly Ser Val Tyr Val
                150                 155                 160 aac aac ttc acg acc atc tcg gac ctc caa tcc gga ggc aat ggc gac      1065
Asn Asn Phe Thr Thr Ile Ser Asp Leu Gln Ser Gly Gly Asn Gly Asp
            165                 170                 175 gta tgg cag ttt tcc acg tct atc ctg gaa ggc ccc aag acc aga cac      1113
Val Trp Gln Phe Ser Thr Ser Ile Leu Glu Gly Pro Lys Thr Arg His
        180                 185                 190 ctg cag ttt cta tcc aca gtc gac tac tgg agg aat ttg ctt gat gca      1161
Leu Gln Phe Leu Ser Thr Val Asp Tyr Trp Arg Asn Leu Leu Asp Ala
    195                 200                 205 gtc aac ggt aaa agc aac gcg ggt ttc aac acc tcg cta act gac tac      1209
Val Asn Gly Lys Ser Asn Ala Gly Phe Asn Thr Ser Leu Thr Asp Tyr
210                 215                 220                 225 tgg ggc cgt gct cta tcc tac cag ttc atc aac gat ccg act ggg aac      1257
Trp Gly Arg Ala Leu Ser Tyr Gln Phe Ile Asn Asp Pro Thr Gly Asn
                230                 235                 240 ggc ggg gtc agc tac acc tgg tcg tcc atc gcc ttg aac gac agc ttc      1305
Gly Gly Val Ser Tyr Thr Trp Ser Ser Ile Ala Leu Asn Asp Ser Phe
            245                 250                 255 cag cgc ggg gag atg cca ctc ccc atc ctg gtc gcg gac ggc cgc aac      1353
Gln Arg Gly Glu Met Pro Leu Pro Ile Leu Val Ala Asp Gly Arg Asn
        260                 265                 270 cca ggc gag cgg ctg atc ggc agc aac tcg acc gtc tac gag ttc aac      1401
Pro Gly Glu Arg Leu Ile Gly Ser Asn Ser Thr Val Tyr Glu Phe Asn
    275                 280                 285 ccg tgg gag ttt ggc tcg ttc gac ccg tcc atc ttc ggc ttt gca ccg      1449
Pro Trp Glu Phe Gly Ser Phe Asp Pro Ser Ile Phe Gly Phe Ala Pro
290                 295                 300                 305
```

```
ctc gag tat ctc ggc tca cgc ttc gac aac ggc cag ctt cct agc ggc      1497
Leu Glu Tyr Leu Gly Ser Arg Phe Asp Asn Gly Gln Leu Pro Ser Gly
        310                 315                 320 gaa tcc tgc gtc cgt ggt ttc gat aat gca ggc ttc gtc atg ggc acc      1545
Glu Ser Cys Val Arg Gly Phe Asp Asn Ala Gly Phe Val Met Gly Thr
            325                 330                 335 tcg tcc tca ctc ttc aac cag ttc atc ctg cgg ctc aac act acc gat      1593
Ser Ser Ser Leu Phe Asn Gln Phe Ile Leu Arg Leu Asn Thr Thr Asp
        340                 345                 350 ctc ccg gac ctg gtc aag gcg gcc ttc tcc agg atc ctc acc gcg cta      1641
Leu Pro Asp Leu Val Lys Ala Ala Phe Ser Arg Ile Leu Thr Ala Leu
    355                 360                 365 ggt cgg gat ggc gac gat atc gcc atc tac gcc ccc aac ccg ttc tac      1689
Gly Arg Asp Gly Asp Asp Ile Ala Ile Tyr Ala Pro Asn Pro Phe Tyr
370                 375                 380                 385 ggg tat cgc aac tcg acc gcg gtc tac tcg cac agc cgc gag ctc gac      1737
Gly Tyr Arg Asn Ser Thr Ala Val Tyr Ser His Ser Arg Glu Leu Asp
                390                 395                 400 gtc gtc gac ggc ggc gag gac ggc cag aat atc ccc tta cac ccc ctc      1785
Val Val Asp Gly Gly Glu Asp Gly Gln Asn Ile Pro Leu His Pro Leu
            405                 410                 415 atc cag cca acc cgc cac gtc gac gtg atc ttc gcg gtt gac tcc tcg      1833
Ile Gln Pro Thr Arg His Val Asp Val Ile Phe Ala Val Asp Ser Ser
        420                 425                 430 gcc gac acg gcg tac aac tgg ccg aat ggg acc tcg cta gtc gcg acc      1881
Ala Asp Thr Ala Tyr Asn Trp Pro Asn Gly Thr Ser Leu Val Ala Thr
    435                 440                 445 tac gag cga agc ctc aac agc tcg gga atc ggc aat agg acg gtc ttc      1929
Tyr Glu Arg Ser Leu Asn Ser Ser Gly Ile Gly Asn Arg Thr Val Phe
450                 455                 460                 465 ccc gcc gtg ccg gac gtg aac acc ttc gtc aac ctg ggc ttg aac acc      1977
Pro Ala Val Pro Asp Val Asn Thr Phe Val Asn Leu Gly Leu Asn Thr
                470                 475                 480 aga ccg acc ttc ttc ggg tgc gat ccc gcg aat ctg tcg gcg ccg gcg      2025
Arg Pro Thr Phe Phe Gly Cys Asp Pro Ala Asn Leu Ser Ala Pro Ala
            485                 490                 495 ccc ttg gtg gta tac ctg ccg aat gcg ccg tac agc gcg cat agc aac      2073
Pro Leu Val Val Tyr Leu Pro Asn Ala Pro Tyr Ser Ala His Ser Asn
        500                 505                 510 acc tcc acc ttc cag ttg tcg tac gcg gat tcc cag cgc gat gag atc      2121
Thr Ser Thr Phe Gln Leu Ser Tyr Ala Asp Ser Gln Arg Asp Glu Ile
    515                 520                 525 atc acg aat ggg tat aac gtt gtg acg cgg ggg aat gca acc gcc gac      2169
Ile Thr Asn Gly Tyr Asn Val Val Thr Arg Gly Asn Ala Thr Ala Asp
530                 535                 540                 545 aag gcc tgg ccg agc tgt gtg ggg tgt gcc att ctg cag cgg tcg atg      2217
Lys Ala Trp Pro Ser Cys Val Gly Cys Ala Ile Leu Gln Arg Ser Met
                550                 555                 560 tat cgg acc aac acg tcc atg ccg gcg gtg tgt tcc agt tgc ttc aag      2265
Tyr Arg Thr Asn Thr Ser Met Pro Ala Val Cys Ser Ser Cys Phe Lys
            565                 570                 575 gcg tat tgc tgg aac ggg acg gtg gat agc aag act cct cgg act tat      2313
Ala Tyr Cys Trp Asn Gly Thr Val Asp Ser Lys Thr Pro Arg Thr Tyr
        580                 585                 590 gag ccg agc cag gtg gtg ggg agt aag tcc acg tct gcg gct tac agg      2361
Glu Pro Ser Gln Val Val Gly Ser Lys Ser Thr Ser Ala Ala Tyr Arg
    595                 600                 605 gag ggt tgaattggct ggtgggcggg tttgctgttg ggctgggagt gtggacagtt       2417
Glu Gly
610
```

```
tagacagatg gcataaatct atctcgctgt tatttgcgcc atctactcgc tagcacctct    2477
tccgtatact gtaggtgcta gcatcccggg                                    2507
```

<210> SEQ ID NO 2
<211> LENGTH: 611
<212> TYPE: PRT
<213> ORGANISM: Aspergillus fumigatus

<400> SEQUENCE: 2

```
Met Lys Ala Ile Phe Thr Leu Leu Thr Ala Leu Ala Val Thr Ala Thr
1               5                   10                  15

Pro Leu Asp Leu Ser Ile Arg Ala Leu Pro Asn Ala Pro Asn Gly Tyr
            20                  25                  30

Thr Pro Ala Asn Val Ser Cys Pro Ala Thr Arg Pro Ser Ile Arg Gly
        35                  40                  45

Ala Gly Ser Leu Ser Pro Asn Glu Thr Ala Trp Leu Gln Ile Arg Arg
    50                  55                  60

Asn Asn Thr Val Gln Pro Met Lys Asp Leu Leu Gly Arg Leu Asn Leu
65                  70                  75                  80

Thr Phe Asp Ala Ala Ser Tyr Ile Asp Arg Val Ser Ser Asn Val Ser
                85                  90                  95

Asn Leu Pro Asn Ile Ala Ile Ala Val Ser Gly Gly Gly Tyr Arg Ala
            100                 105                 110

Leu Thr Asn Gly Ala Gly Ala Ile Lys Ala Phe Asp Asn Arg Thr Lys
        115                 120                 125

Gly Ser Thr Ala Pro Gly Gln Leu Gly Gly Leu Gln Ser Ala Thr
    130                 135                 140

Tyr Val Ser Gly Leu Ser Gly Gly Gly Trp Leu Val Gly Ser Val Tyr
145                 150                 155                 160

Val Asn Asn Phe Thr Thr Ile Ser Asp Leu Gln Ser Gly Gly Asn Gly
                165                 170                 175

Asp Val Trp Gln Phe Ser Thr Ser Ile Leu Glu Gly Pro Lys Thr Arg
            180                 185                 190

His Leu Gln Phe Leu Ser Thr Val Asp Tyr Trp Arg Asn Leu Leu Asp
        195                 200                 205

Ala Val Asn Gly Lys Ser Asn Ala Gly Phe Asn Thr Ser Leu Thr Asp
    210                 215                 220

Tyr Trp Gly Arg Ala Leu Ser Tyr Gln Phe Ile Asn Asp Pro Thr Gly
225                 230                 235                 240

Asn Gly Gly Val Ser Tyr Thr Trp Ser Ser Ile Ala Leu Asn Asp Ser
                245                 250                 255

Phe Gln Arg Gly Glu Met Pro Leu Pro Ile Leu Val Ala Asp Gly Arg
            260                 265                 270

Asn Pro Gly Glu Arg Leu Ile Gly Ser Asn Ser Thr Val Tyr Glu Phe
        275                 280                 285

Asn Pro Trp Glu Phe Gly Ser Phe Asp Pro Ser Ile Phe Gly Phe Ala
    290                 295                 300

Pro Leu Glu Tyr Leu Gly Ser Arg Phe Asp Asn Gly Gln Leu Pro Ser
305                 310                 315                 320

Gly Glu Ser Cys Val Arg Gly Phe Asp Asn Ala Gly Phe Val Met Gly
                325                 330                 335

Thr Ser Ser Ser Leu Phe Asn Gln Phe Ile Leu Arg Leu Asn Thr Thr
            340                 345                 350

Asp Leu Pro Asp Leu Val Lys Ala Ala Phe Ser Arg Ile Leu Thr Ala
        355                 360                 365
```

Leu Gly Arg Asp Gly Asp Ile Ala Ile Tyr Ala Pro Asn Pro Phe
    370                 375                 380

Tyr Gly Tyr Arg Asn Ser Thr Ala Val Tyr Ser His Ser Arg Glu Leu
385                 390                 395                 400

Asp Val Val Asp Gly Gly Glu Asp Gly Gln Asn Ile Pro Leu His Pro
                405                 410                 415

Leu Ile Gln Pro Thr Arg His Val Asp Val Ile Phe Ala Val Asp Ser
            420                 425                 430

Ser Ala Asp Thr Ala Tyr Asn Trp Pro Asn Gly Thr Ser Leu Val Ala
        435                 440                 445

Thr Tyr Glu Arg Ser Leu Asn Ser Ser Gly Ile Gly Asn Arg Thr Val
    450                 455                 460

Phe Pro Ala Val Pro Asp Val Asn Thr Phe Val Asn Leu Gly Leu Asn
465                 470                 475                 480

Thr Arg Pro Thr Phe Phe Gly Cys Asp Pro Ala Asn Leu Ser Ala Pro
                485                 490                 495

Ala Pro Leu Val Val Tyr Leu Pro Asn Ala Pro Tyr Ser Ala His Ser
            500                 505                 510

Asn Thr Ser Thr Phe Gln Leu Ser Tyr Ala Asp Ser Gln Arg Asp Glu
        515                 520                 525

Ile Ile Thr Asn Gly Tyr Asn Val Val Thr Arg Gly Asn Ala Thr Ala
    530                 535                 540

Asp Lys Ala Trp Pro Ser Cys Val Gly Cys Ala Ile Leu Gln Arg Ser
545                 550                 555                 560

Met Tyr Arg Thr Asn Thr Ser Met Pro Ala Val Cys Ser Ser Cys Phe
                565                 570                 575

Lys Ala Tyr Cys Trp Asn Gly Thr Val Asp Ser Lys Thr Pro Arg Thr
            580                 585                 590

Tyr Glu Pro Ser Gln Val Val Gly Ser Lys Thr Ser Ala Ala Tyr
        595                 600                 605

Arg Glu Gly
    610

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gactcgagtc gacatcgatt tttttttttt tttttttv                          39

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatggcggcg aggatggaca gaa                                          23

<210> SEQ ID NO 5
<211> LENGTH: 18
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 5
agtgccgttc cagcaata                                                       18

<210> SEQ ID NO 6
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaattccgcg gactgcgcat catgaaggcc attttcaccc ttctgac                       47

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgaggatcct ggagaaggcc gccttg                                              26

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atgggcacct cgtcctcact cttc                                                24

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgggatccta gcacctacag tatacggaag                                          30
```